US010722109B2

(12) United States Patent
Kermani

(10) Patent No.: US 10,722,109 B2
(45) Date of Patent: Jul. 28, 2020

(54) APPARATUS AND METHOD TO ILLUMINATE AND ORIENT GUIDEWIRE

(71) Applicant: Acclarent, Inc., Irvine, CA (US)

(72) Inventor: Mahyar Z. Kermani, San Ramon, CA (US)

(73) Assignee: Acclarent, Inc., Irvine, CA (US)

( * ) Notice: Subject to any disclaimer, the term of this patent is extended or adjusted under 35 U.S.C. 154(b) by 150 days.

(21) Appl. No.: 16/139,606

(22) Filed: Sep. 24, 2018

(65) Prior Publication Data
US 2019/0090730 A1 Mar. 28, 2019

Related U.S. Application Data

(63) Continuation of application No. 14/834,936, filed on Aug. 25, 2015, now Pat. No. 10,123,685.

(51) Int. Cl.
*A61B 1/233* (2006.01)
*A61B 1/07* (2006.01)
(Continued)

(52) U.S. Cl.
CPC .......... *A61B 1/233* (2013.01); *A61B 1/00186* (2013.01); *A61B 1/0684* (2013.01); *A61B 1/07* (2013.01); *A61B 5/0084* (2013.01); *A61B 17/24* (2013.01); *A61M 25/09* (2013.01); *A61B 2017/00907* (2013.01); *A61B 2017/22038* (2013.01); *A61B 2017/22042* (2013.01); *A61B 2090/0811* (2016.02); *A61B 2090/306* (2016.02); *A61B 2090/3945* (2016.02);
(Continued)

(58) Field of Classification Search
CPC ....... A61B 1/233; A61B 17/24; A61B 17/885; A61B 17/8852; A61B 17/8855; A61B 17/8858; A61B 2017/246; A61B 25/09; A61B 2025/09008; A61B 2025/09041
See application file for complete search history.

(56) References Cited

U.S. PATENT DOCUMENTS 5,105,818 A * 4/1992 Christian .................. A61B 8/06
600/463
5,163,445 A * 11/1992 Christian .................. A61B 8/06
248/623

(Continued)

OTHER PUBLICATIONS

European Office Action dated Nov. 28, 2018 for Application No. 16751412.4, 4 pages.

(Continued)

*Primary Examiner* — Eric S Gibson
(74) *Attorney, Agent, or Firm* — Frost Brown Todd LLC

(57) ABSTRACT

An apparatus includes a power source, a pulse generator, a light source, a guidewire, an optical fiber, and a connector. The pulse generator is in electrical communication with the power source. The pulse generator is also capable of generating an electric pulse. The light source is in electrical communication with the pulse generator in such a way that the light source turns on and off in response to the electric pulse received from the pulse generator. The guidewire includes a proximal end and a distal end. The optical fiber extends through the guidewire from the proximal end of the guidewire towards the distal end of the guidewire. The connector couples with the guidewire while allowing the light source to communicate with the optical fiber.

20 Claims, 23 Drawing Sheets

(51) Int. Cl.

| | | |
|---|---|---|
| *A61B 1/06* | (2006.01) | |
| *A61B 1/00* | (2006.01) | |
| *A61B 17/24* | (2006.01) | |
| *A61B 5/00* | (2006.01) | |
| *A61M 25/09* | (2006.01) | |
| *A61B 90/00* | (2016.01) | |
| *A61B 17/00* | (2006.01) | |
| *A61B 17/22* | (2006.01) | |
| *A61B 90/30* | (2016.01) | |
| *A61M 25/00* | (2006.01) | |
| *A61M 25/06* | (2006.01) | |
| *A61M 29/02* | (2006.01) | |

(52) U.S. Cl.
CPC ......... *A61M 25/0041* (2013.01); *A61M 29/02* (2013.01); *A61M 2025/0681* (2013.01)

(56) References Cited

U.S. PATENT DOCUMENTS

| | | | | |
|---|---|---|---|---|
| 5,174,295 | A * | 12/1992 | Christian | A61B 8/06 600/468 |
| 9,155,492 | B2 * | 10/2015 | Jenkins | A61B 5/065 |
| 9,314,374 | B2 * | 4/2016 | Artsyukhovich | A61B 90/20 |
| 9,554,817 | B2 * | 1/2017 | Goldfarb | A61M 29/00 |
| 9,579,448 | B2 * | 2/2017 | Chow | A61M 25/1018 |
| 9,962,530 | B2 | 5/2018 | Johnson et al. | |
| 10,123,685 | B2 | 11/2018 | Kermani | |
| 2008/0183128 | A1 | 7/2008 | Morriss et al. | |
| 2009/0156999 | A1 * | 6/2009 | Adams | A61M 25/005 604/103.09 |
| 2010/0030031 | A1 * | 2/2010 | Goldfarb | A61B 1/00183 600/163 |
| 2011/0004057 | A1 * | 1/2011 | Goldfarb | A61M 29/02 600/106 |
| 2011/0230728 | A1 * | 9/2011 | Artsyukhovich | A61F 9/00745 600/249 |
| 2012/0078118 | A1 * | 3/2012 | Jenkins | A61B 17/24 600/478 |
| 2014/0074141 | A1 * | 3/2014 | Johnson | A61M 25/10182 606/192 |
| 2014/0275775 | A1 * | 9/2014 | Jones | A61M 25/09041 600/109 |
| 2017/0055818 | A1 * | 3/2017 | Kermani | A61B 5/0084 |
| 2019/0090730 | A1 * | 3/2019 | Kermani | A61B 1/07 |

OTHER PUBLICATIONS

International Search Report and Written Opinion dated Jan. 25, 2017 for Application No. PCT/US2016/044488, 14 pgs.
U.S. Pat. No. 10,123,685.
Chinese Office Action and Search Report dated Oct. 10, 2019 for Application No. 201680062501.X, 16 pages.
European Communication dated Jun. 26, 2019 for Application No. 16751412.4, 3 pages.

* cited by examiner

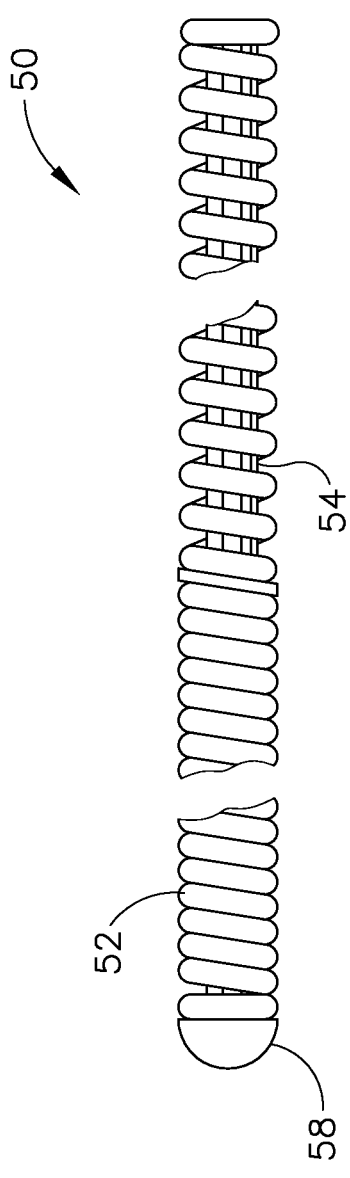
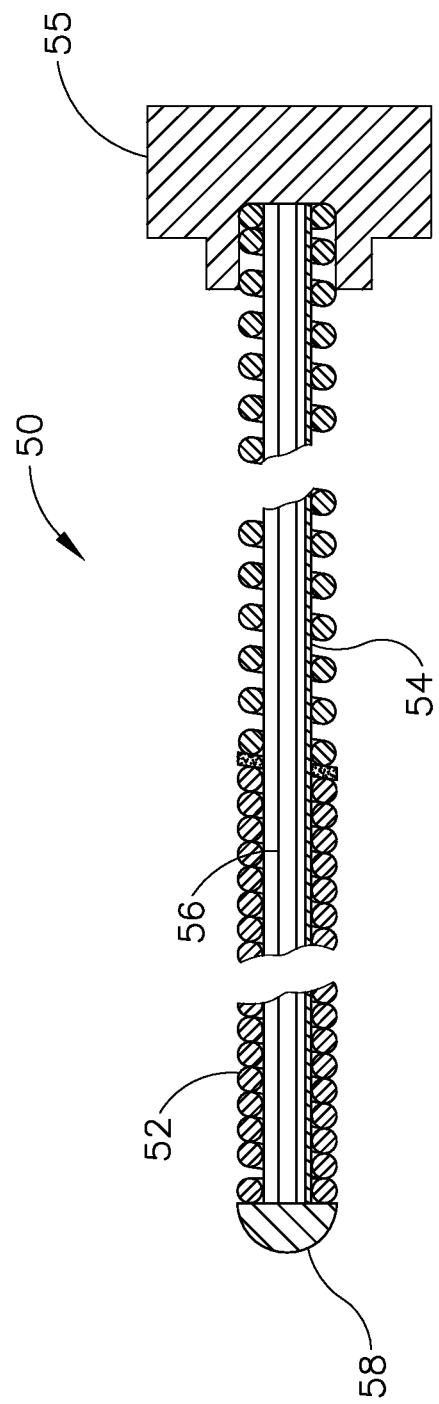
Fig. 3
Fig. 4

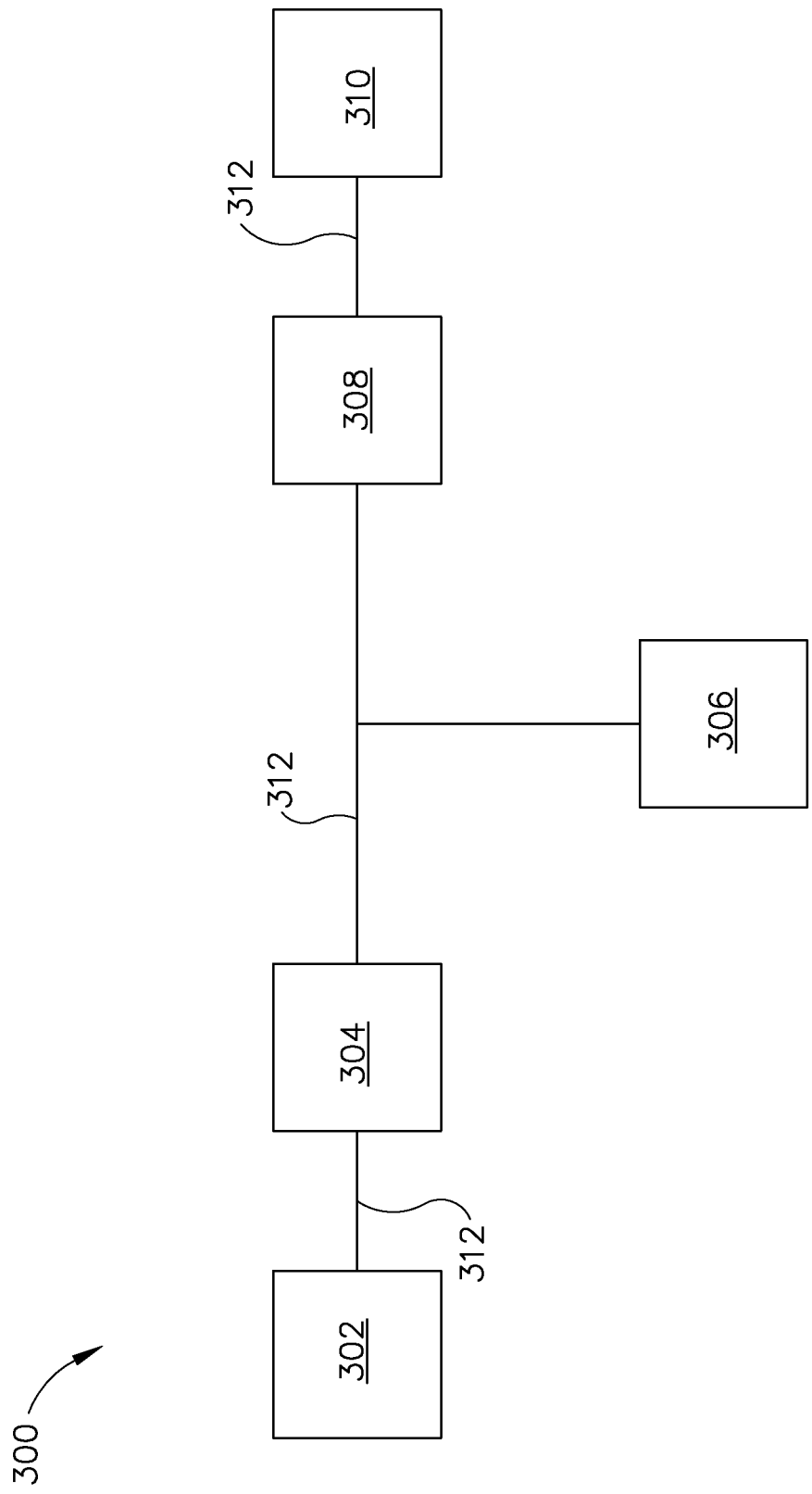

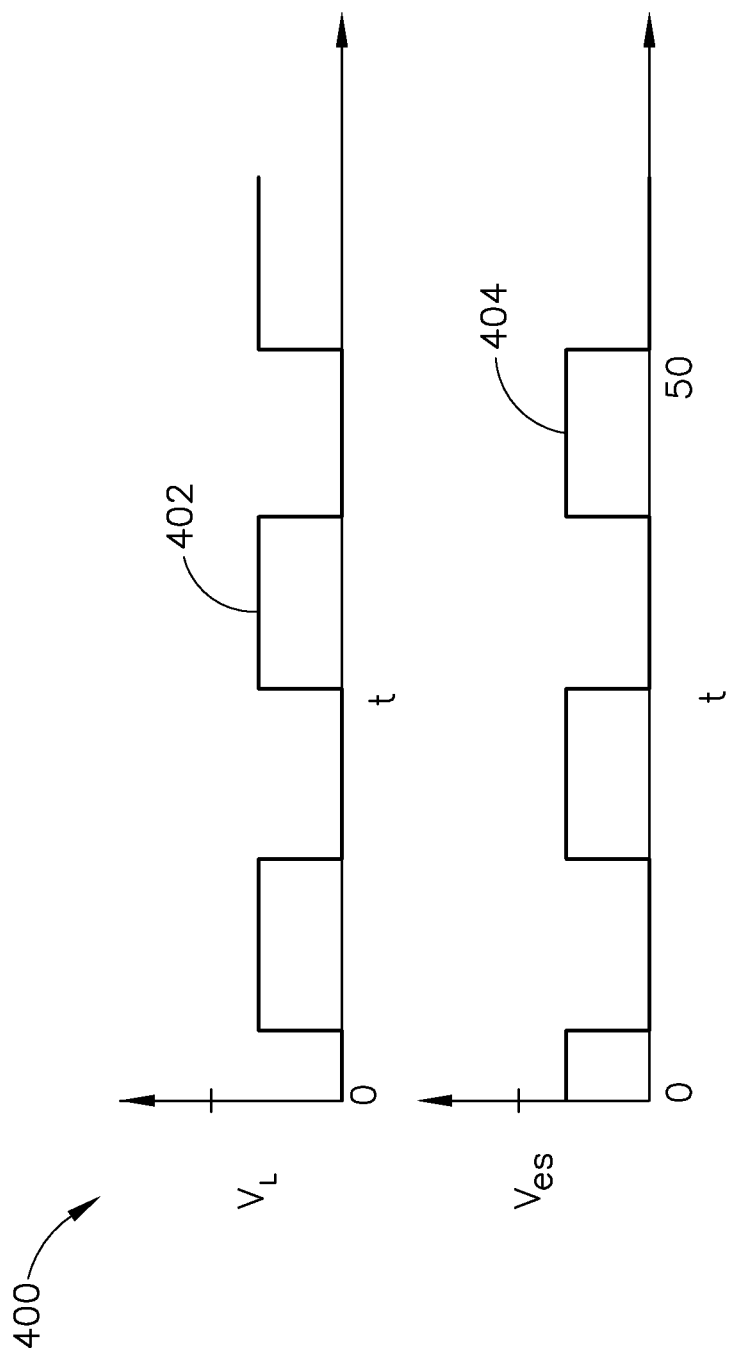

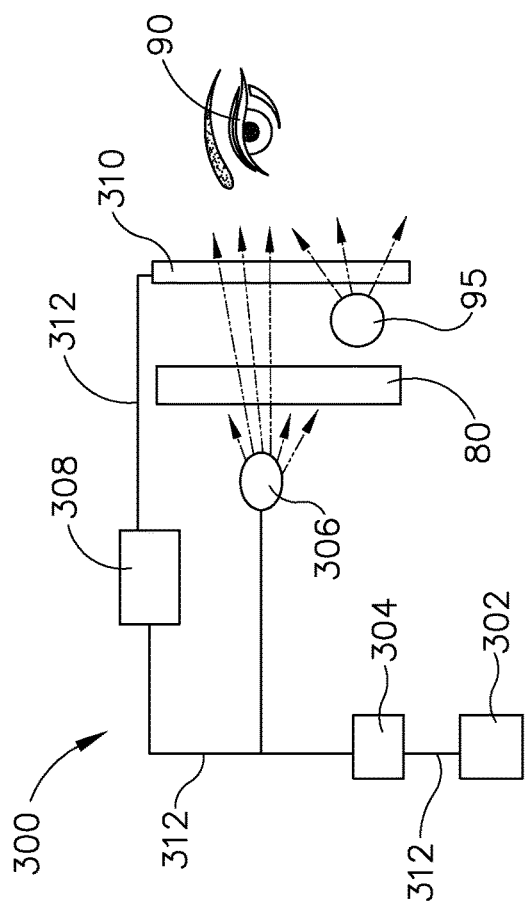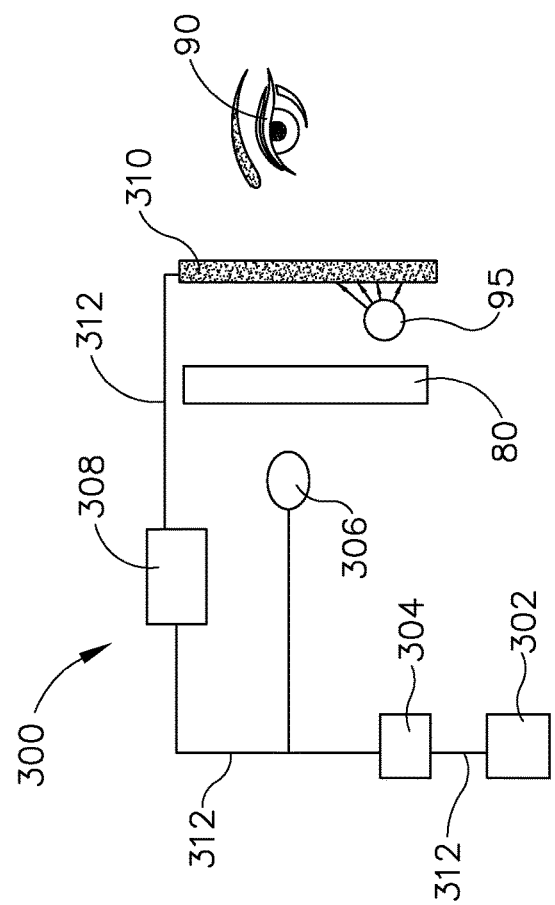

derma, subdermis, etc.) and thus
APPARATUS AND METHOD TO ILLUMINATE AND ORIENT GUIDEWIRE This application is a continuation of U.S. patent application Ser. No. 14/834,936, entitled "Apparatus and Method to Illuminate and Orient Guidewire," filed Aug. 25, 2015, issued as U.S. Pat. No. 10,123,685 on Nov. 13, 2018.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide transcutaneous illumination that is more easily visible in relation to ambient light. While several systems and methods have been made to illuminate guidewire, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guidewire of FIG. 2A;

FIG. 4 depicts a detailed side cross-sectional view of the illuminating guidewire of FIG. 2A;

FIG. 14 depicts a schematic diagram of a synchronized illumination viewing device, which may be used with the illuminating guidewire system of FIG. 13;

FIG. 15 depicts a graph showing the voltage consumption of both the light source and the electronic shutter of the synchronized illumination viewing device of FIG. 14 as a function of time;

FIG. 16A depicts a schematic diagram of the synchronized illumination viewing device of FIG. 14 being used during a procedure with the light source activated and the electronic shutter open;

FIG. 16B depicts a schematic diagram of the synchronized illumination viewing device of FIG. 14 being used during a procedure with the light source deactivated and the electronic shutter closed;

Figure 1:
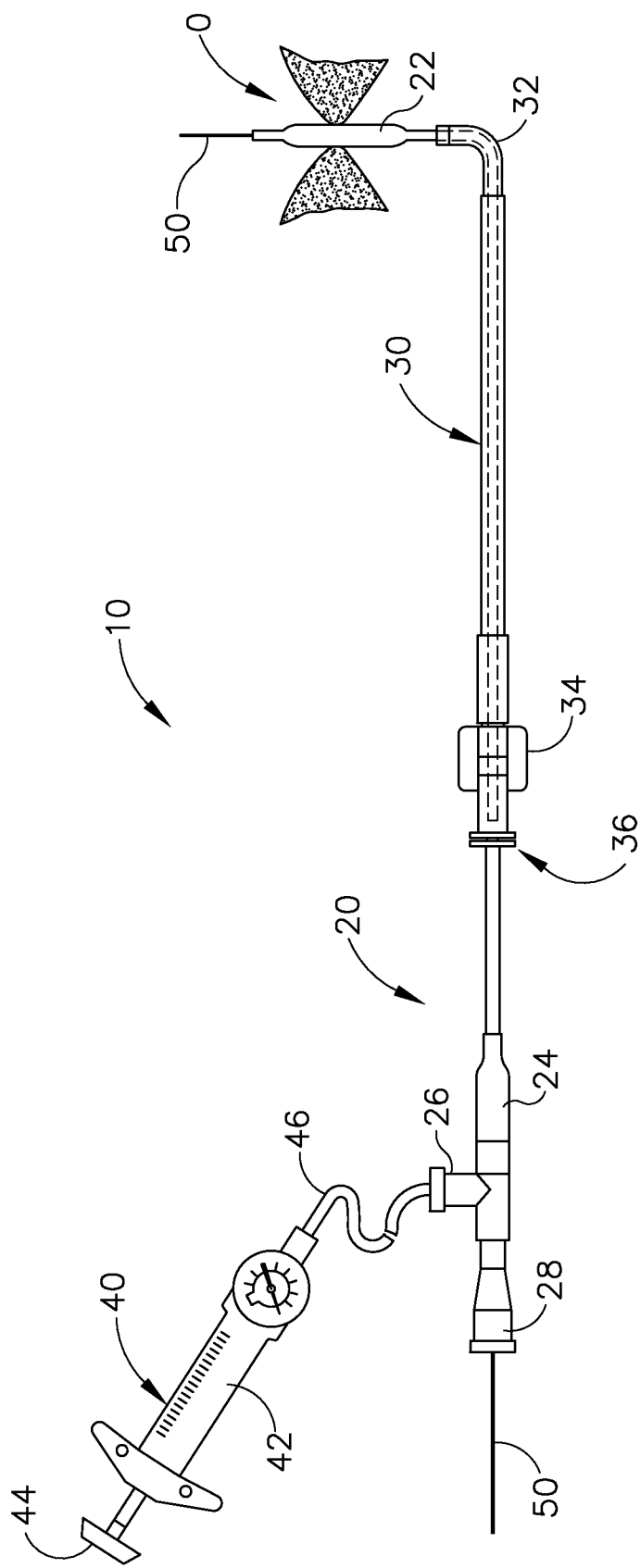
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
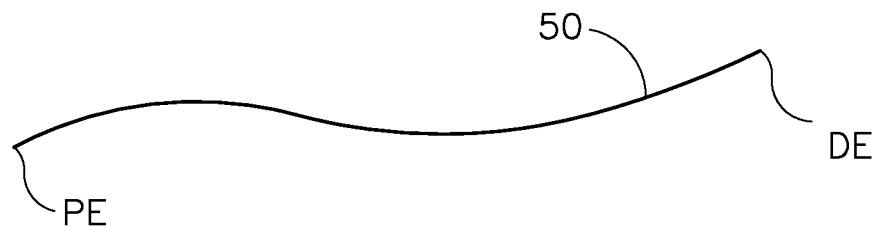
FIG. 2A depicts a side elevational view of an exemplary illuminating guidewire of the dilation catheter system of FIG. 1.
Figure 2B:
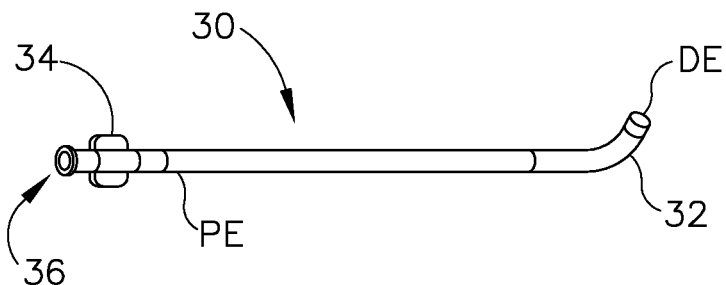
FIG. 2B depicts a side elevational view of an exemplary guide catheter of the dilation catheter system of FIG. 1.
Figure 2C:
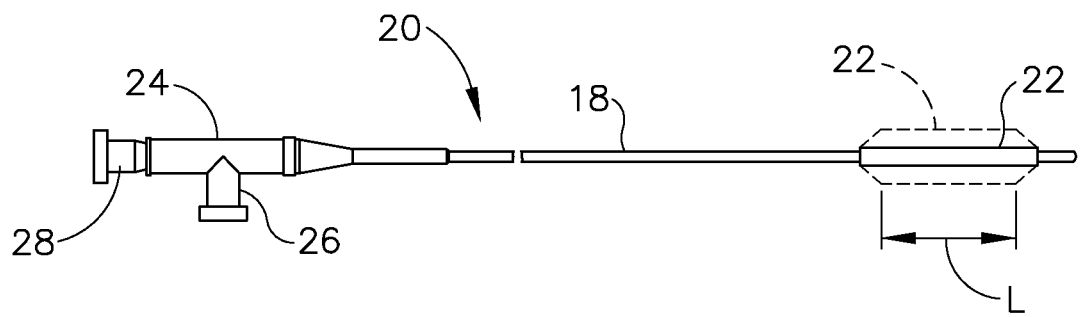
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20)

may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, now U.S. Pat. No. 9,962,530, issued May 8, 2018, the disclosure of which is incorporated by reference herein.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

Figure 5:
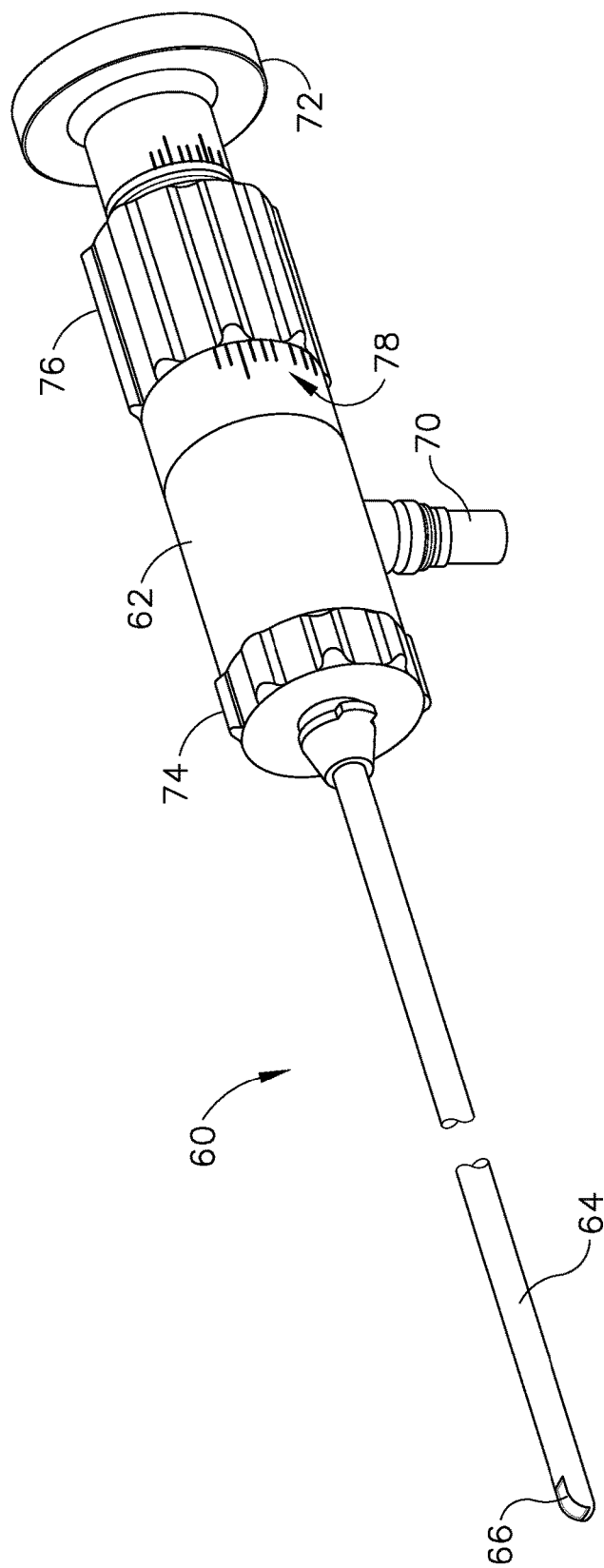
FIG. 5 depicts a perspective view of an exemplary endoscope suitable for use with the dilation catheter system of FIG. 1.
Figure 6:
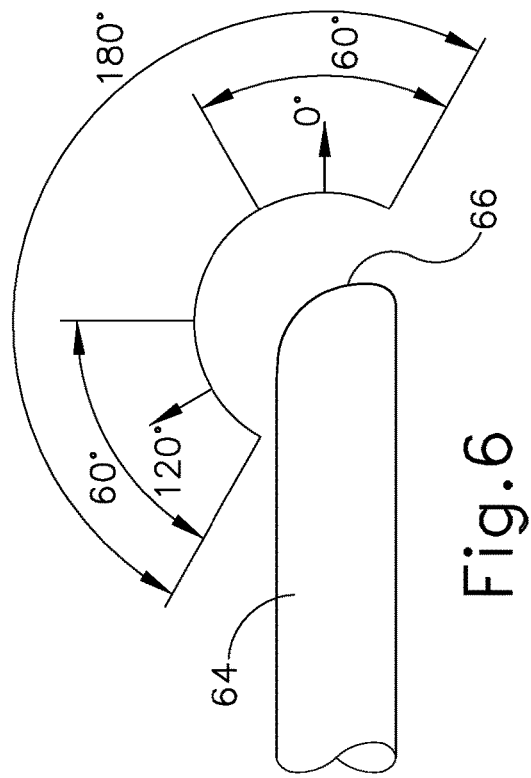
FIG. 6 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 5-6, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein

III. Exemplary Method for Dilating the Ostium of a Maxillary Sinus

FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
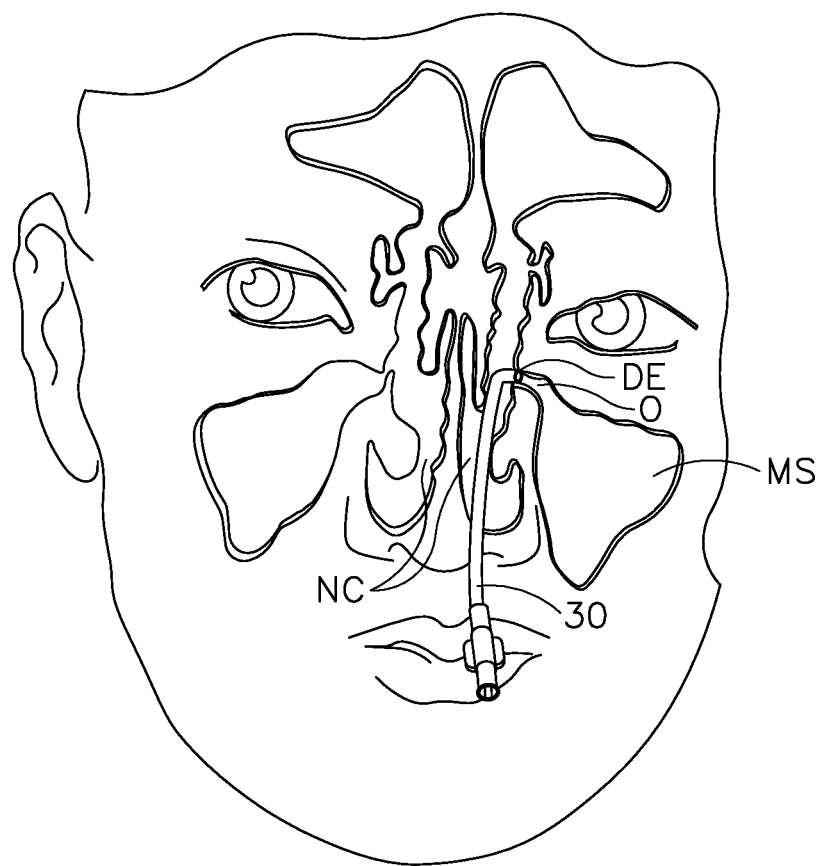
FIG. 7A depicts a front view of the guide catheter of FIG. 2B positioned adjacent an ostium of the maxillary sinus.
Figure 7C:
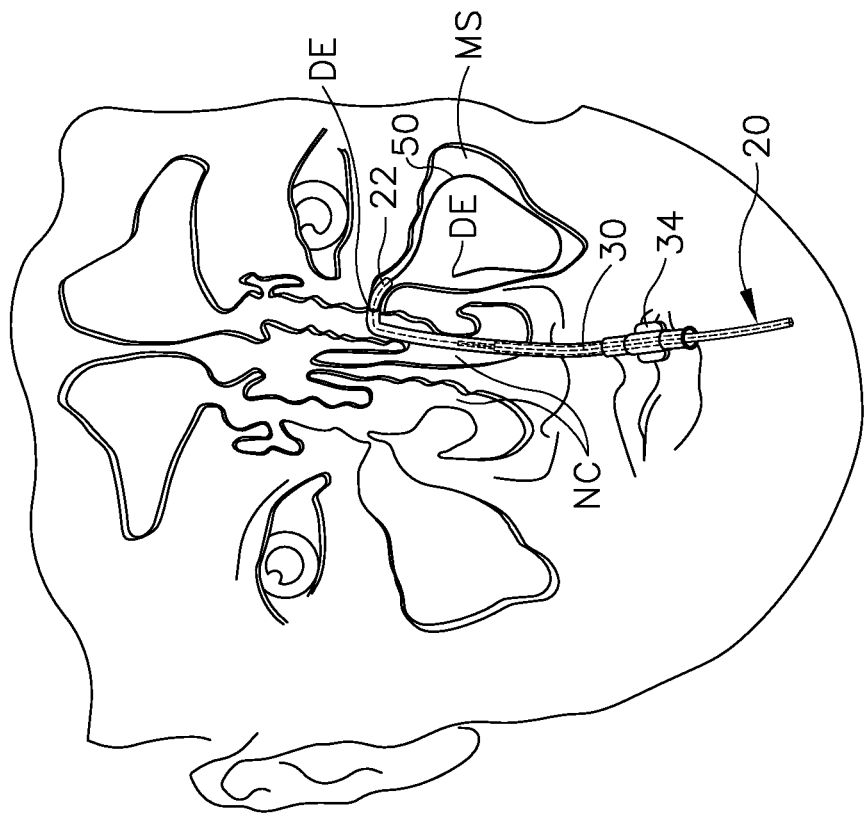
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
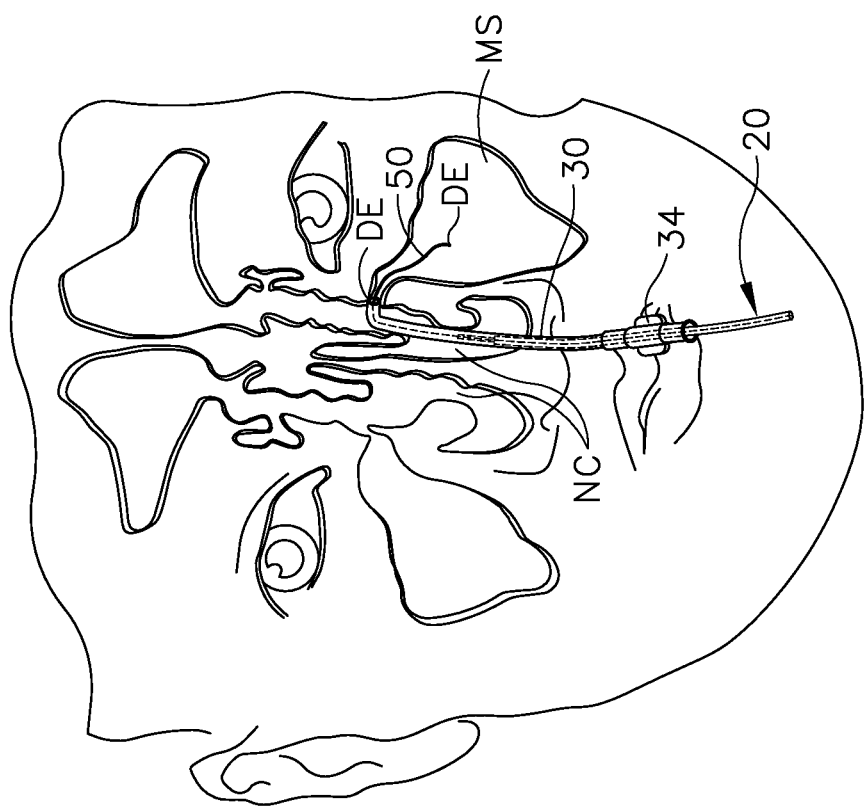
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
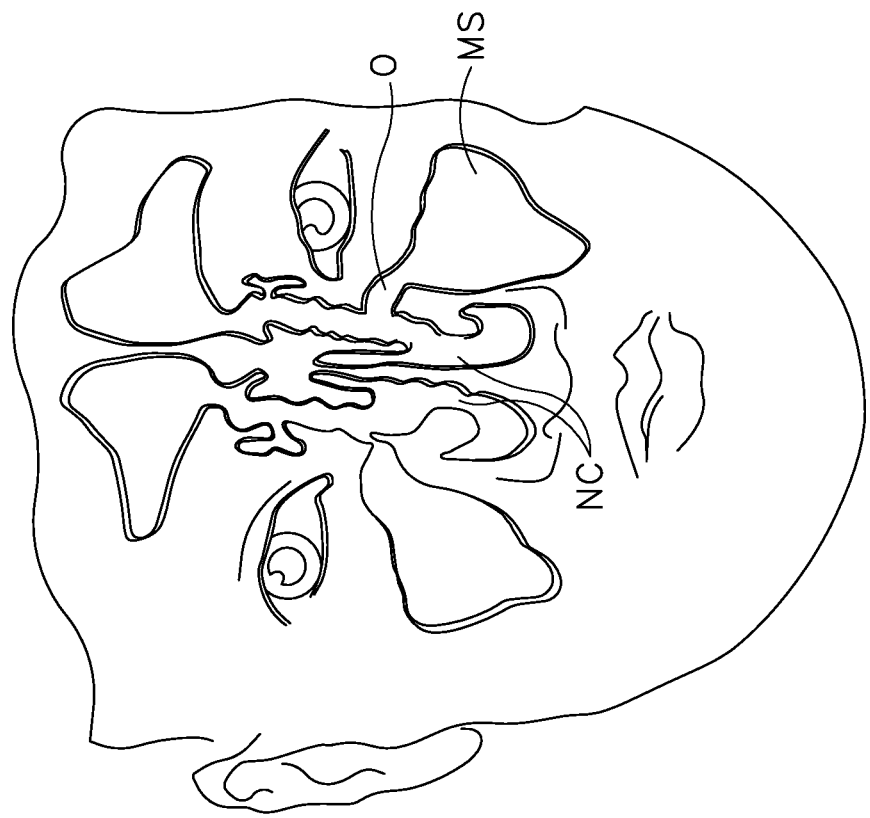
FIG. 7E depicts a front view of an ostium of the maxillary sinus, with the ostium having been enlarged by inflation of the balloon of FIG. 7D.
Figure 7D:
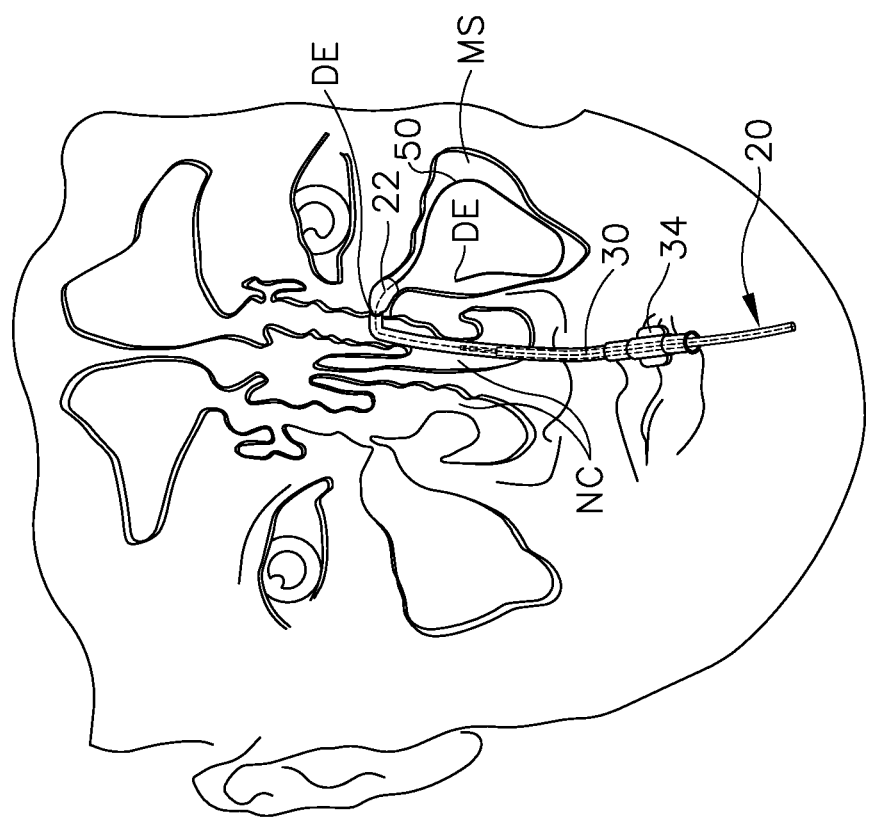
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (0). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128 U.S. Pat. No. 7,630,676, entitled "Methods, Devices and Systems for Treatment and/or Diagnosis of Disorders of the Ear, Nose and Throat," published Jul. 31, 2008. An example of an irrigation catheter that may be fed through guide catheter (30) to reach the irrigation site after removal of dilation catheter (20) is the Relieva Vortex®. Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra®. Sinus Irrigation Catheter by Acclarent, Inc. of Menlo Park, Calif. Of course, irrigation may be provided in the absence of a dilation procedure; and a dilation procedure may be completed without also including irrigation.

IV. Alternative Light Sources for Guidewires

In some instances, in the procedure referenced above, a continuous source of "white light" (light composed of a mixture of colors of light with many different wavelengths) is utilized to illuminate illumination fiber (56) and lens (58) for providing transcutaneous illumination through the patient's face, thereby enabling the operator to visually confirm positioning of the distal end of guidewire (50) within a patient. However, an operator may have difficulty visualizing the transcutaneous illumination caused by the illumination fiber (56) and lens (58) due to various factors such as, but not limited to, source of high ambient light in relation to illumination fiber (56), adaptation of the eye to light sources, various absorption coefficients related to specific patients, and an undesirable wavelength utilized by light source. Utilizing some of the following teachings may assist an operator in detecting transcutaneous illumination from a variation of guidewire (50).

A. Light Source with Optimized Wavelength

Figure 8:
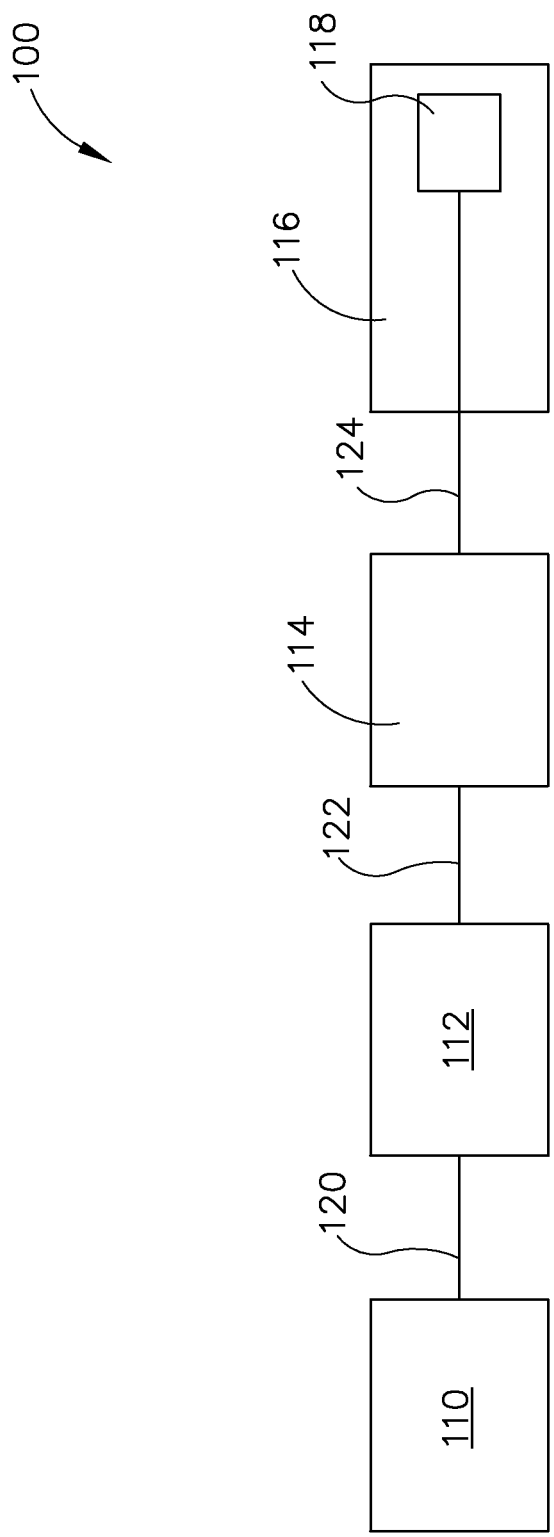
FIG. 8 depicts a schematic diagram of an exemplary illuminating guidewire system that may be incorporated into the dilation catheter system of FIG. 1.

FIG. 8 shows an exemplary illuminating guidewire system (100), which includes a power source (110), a light source (112), a connector (114), a guidewire (116), and an illumination fiber (124) traveling through guidewire (116) and connecting to optical lens (118) located at the distal end of guidewire (116). Power source (110) is connected to light source (112) by electrical wiring (120), such that power source (110) is operable to provide the proper amount of electrical power to activate light source (112). As will be described in greater detail below, light source (112) is capable of generating light with specific wavelengths as well as "white light" mixture of wavelengths. Alternatively, light source (112) may only generate specific wavelengths, without the capabilities of generating "white light." Light source (112) connects to light tube (112), which in turn connects to connector (114). Light tube (112) is capable of communicating light generated by light source (112) to connector (114).

Connector (114) may be substantially similar to connector (55) referenced above. Specifically, connector (114) enables optical coupling of illumination fiber (124) with light source (112) and/or light tube (122). Additionally, connector (114) may also be connected to the proximal end of guidewire (116). Guidewire (116) is substantially similar to guidewire (50) referenced above. Therefore, light generated by light source (112) is capable of traveling through light tube (122), illumination fiber (124), and optical lens (118) to provide transcutaneous illumination through the patient's face to enable an operator to visually confirm positioning of the distal end of guidewire (116) in a patient's sinus cavity. It should therefore be understood that guidewire (116) may be used as a part of dilation catheter system (10) in place of guidewire (50).

As mentioned above, light source (112) is capable of generating light with specific wavelengths rather than with a "white light" mixture of wavelengths. As described in greater detail below, the capability of light source (112) to generate light with specific wavelengths may help maximize the transcutaneous illumination traveling through the patient's face.

Figure 9:
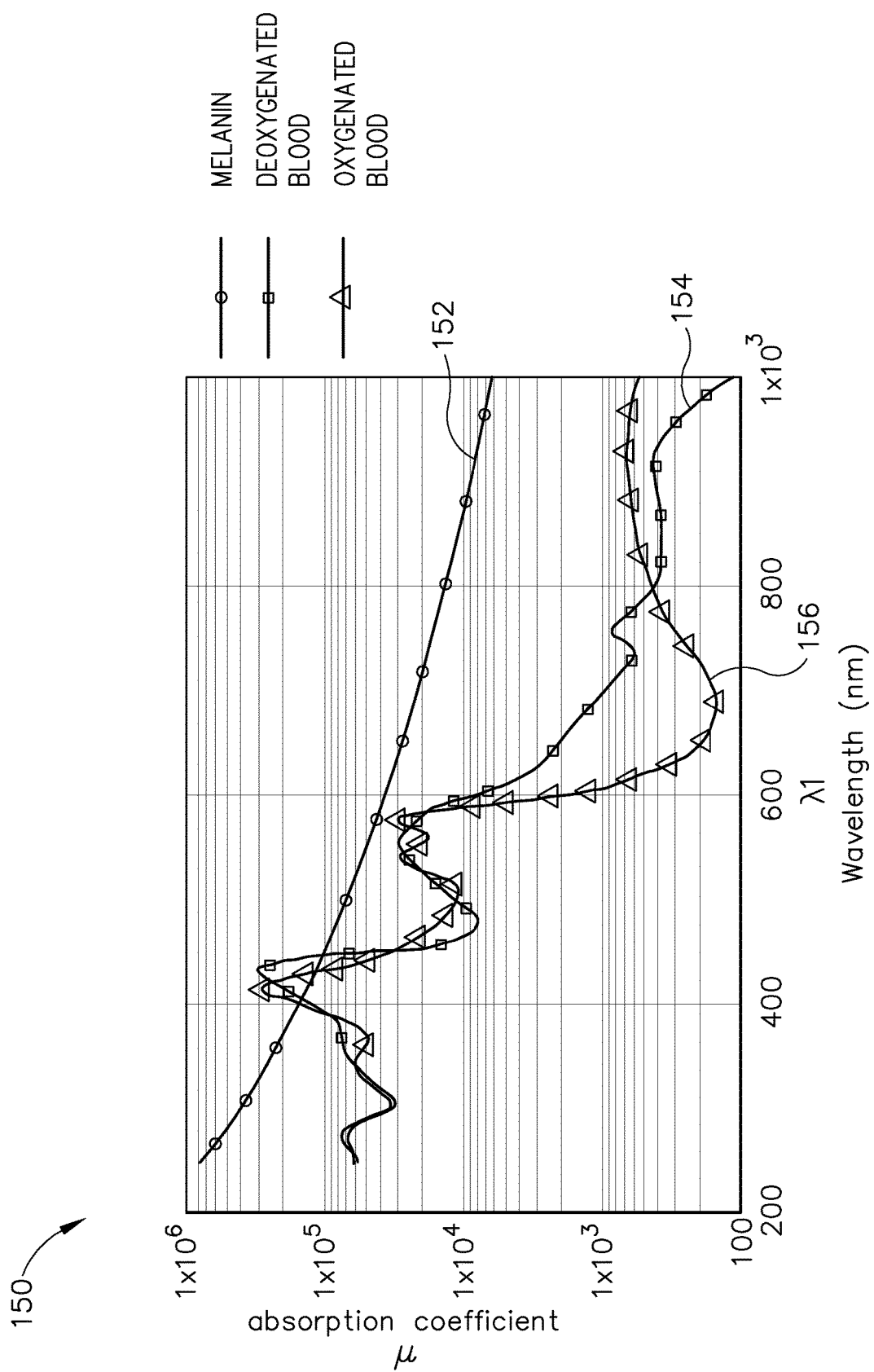
FIG. 9 depicts a graph showing the absorption coefficient of various materials as a function of light wavelength.

There are at least three separate components in the body, especially skin, that provide light absorption—oxygenated blood, deoxygenated blood, and melanin (i.e. skin pigmentation). FIG. 9 shows a graph (150) of the absorption coefficient ($\mu$) for oxygenated blood (156), deoxygenated blood (154), and melanin (152) as a function of a wavelength of light on a logarithmic scale. The absorption coefficient ($0$ represents how far a particular wavelength of light can penetrate into a material until the wavelength of light is absorbed by the material. The lower the absorption coefficient, the further the particular wavelength will travel (i.e. appearing to be more translucent). As can be seen in graph (150) of FIG. 9, the deoxygenated blood (154) and oxygenated blood (156) generally have a decrease in the absorption coefficient ($0$ as the wavelength increases, with some limited exceptions. Melanin (152) seems to have a decrease in absorption coefficient ($0$ as the wavelength increases.

Figure 10:
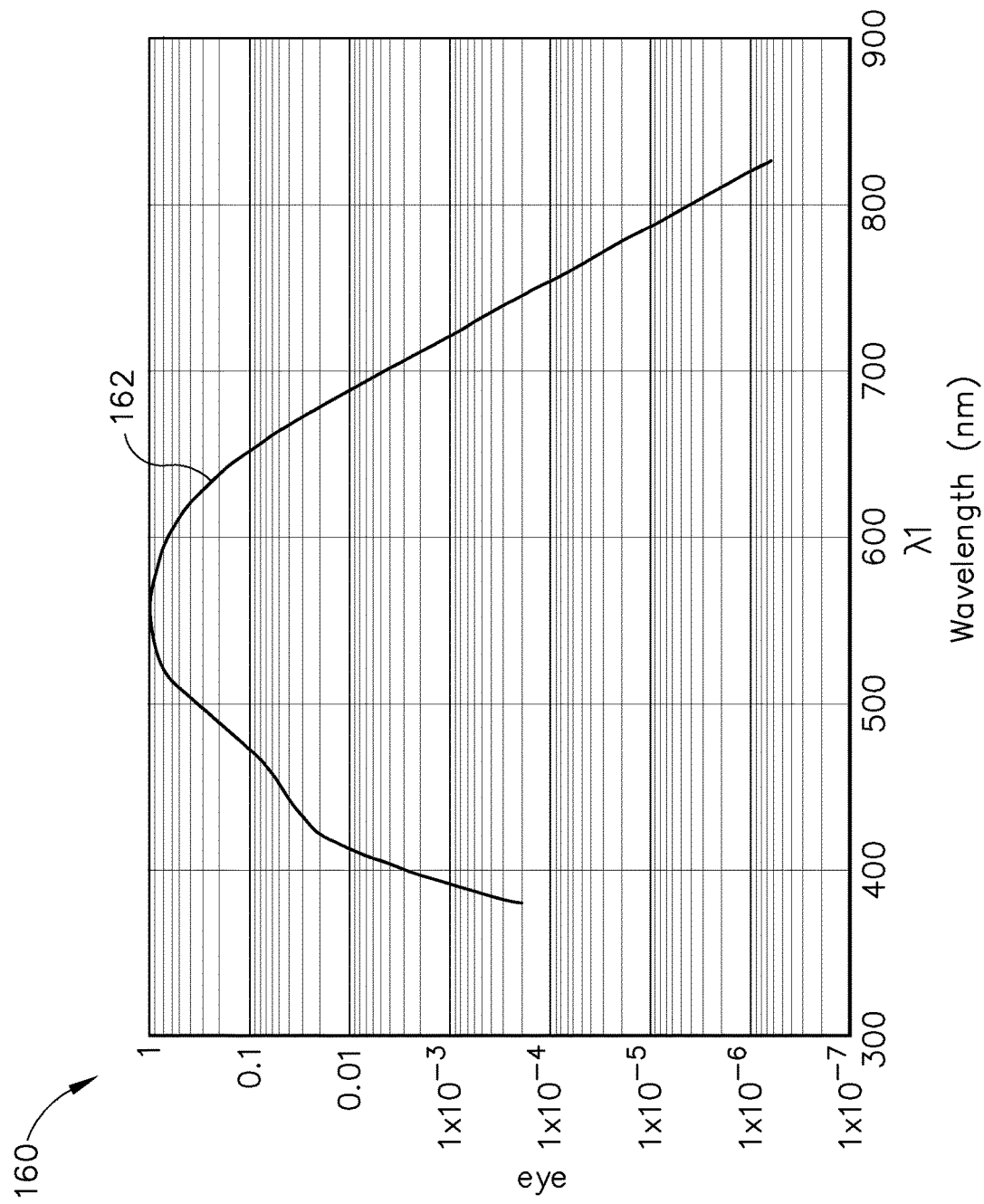
FIG. 10 depicts a graph showing the eye sensitivity as a function of light wavelength.

FIG. 10 shows a graph (160) of the specific response (162) of a human eye as a function of the wavelength of light on a logarithmic scale. In graph (160), the eye response has been normalized to the maximum response around 560 nm. If a wavelength of light has a higher specific response, that wavelength of light would be interpreted by the human eye as brighter than a wavelength of light having a smaller specific response, if both wavelengths of light were projected at the same luminance. Therefore, the higher the specific response (162) of a wavelength of light, the more visible the wavelength of light is to the human eye.

The Beer-Lambert law may be utilized to calculate an estimation of the amount of light traveling through an object. The Beer-Lambert law is the following formula:

$$I = I_o e^{-\Sigma \mu_i D_i}$$

I represents the output light intensity, $I_o$ represents the input light intensity, $\mu_i$ represents the absorption coefficient of material (i), while $D_i$ represents the thickness of material (i).

Figure 11:
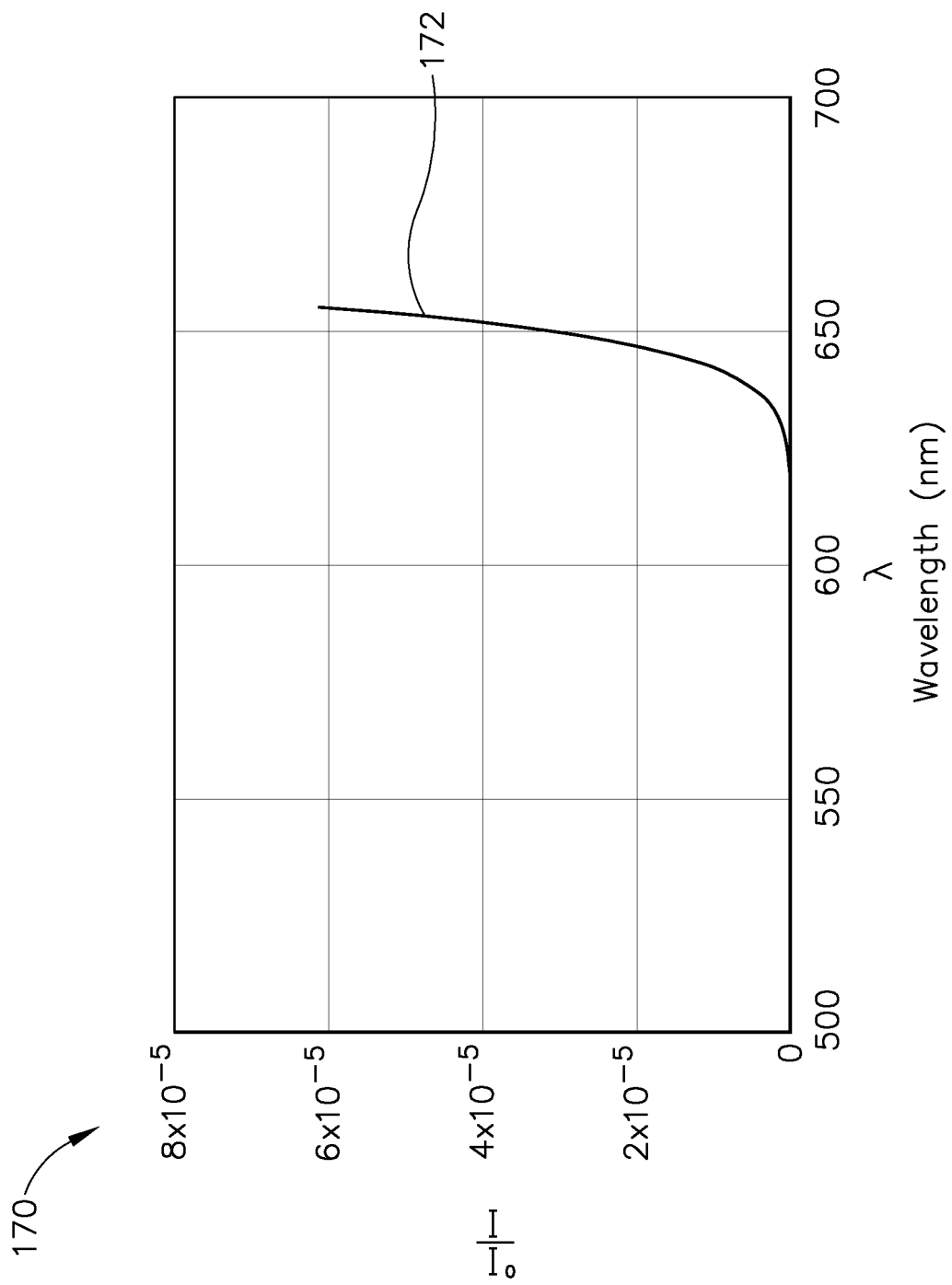
FIG. 11 depicts a graph showing the throughput efficiency of light traveling through a body.

FIG. 11 shows a graph (170) depicting the estimated ratio $I/I_o$ as calculated utilizing Beer-Lambert law with a summation of absorption coefficients ($0$ multiplied by thicknesses (D) of oxygenated blood (156), deoxygenated blood (154), and melanin (152). The ratio $I/I_o$ represents the indication of the light throughput efficiency (172) through the body. As can be seen in FIG. 11, the light throughput efficiency (172) exponentially increases as a function of wavelength.

Figure 12:
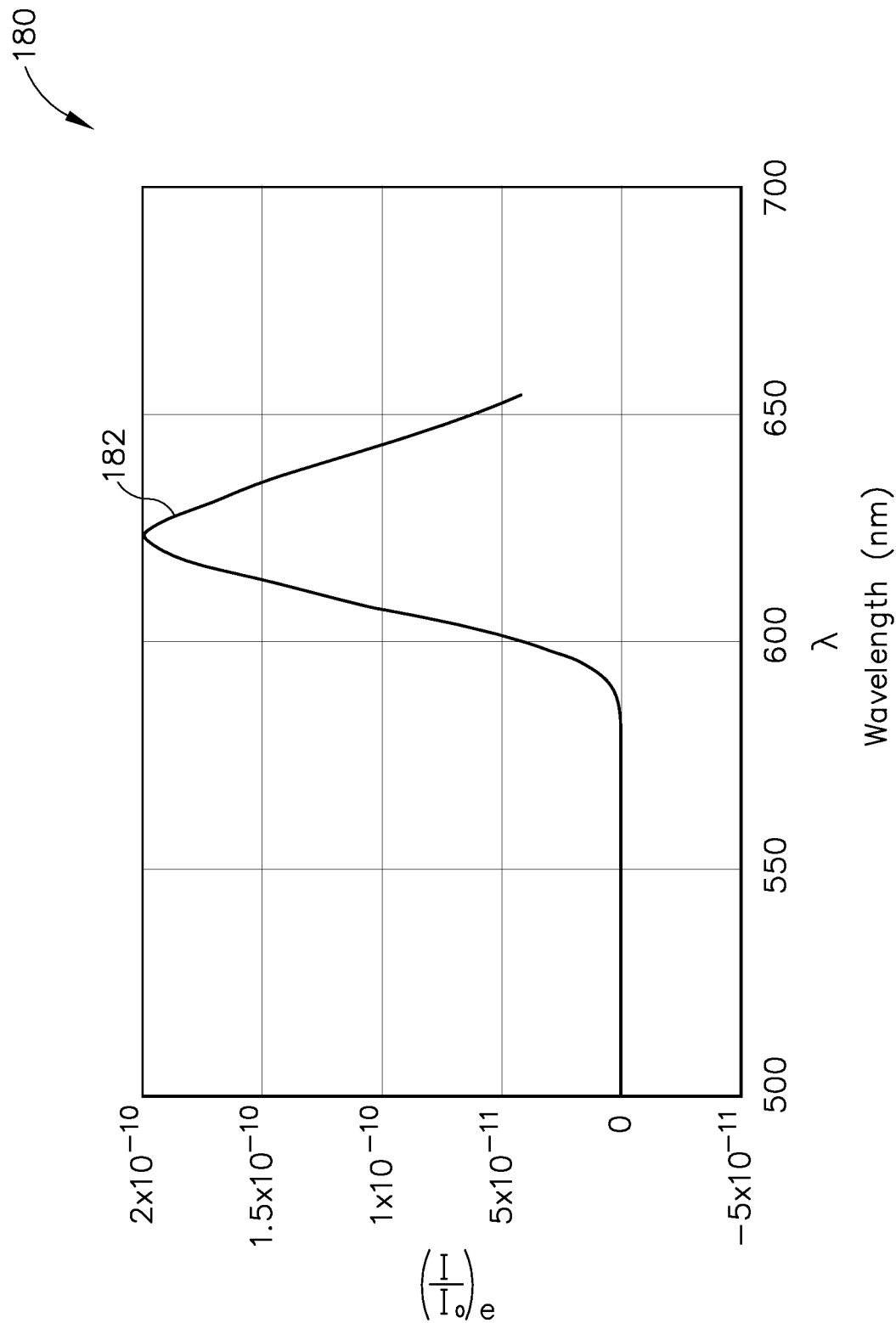
FIG. 12 depicts a graph showing the throughput efficiency of light traveling through a body as masked by the eye response.

However, as noted above, the vision of the human eye is limited by the specific response (162) as shown in graph (160) of FIG. 10. Therefore, even though light with a higher wavelength is capable of traveling through the human body with more efficiency as represented in FIG. 11, the human eye will not be able to detect these wavelengths as effectively as wavelengths with a higher specific response (162). In order to account for the specific response (162) of the human eye, graph (170) must be filtered by graph (160). FIG. 12 shows a graph (180) depicting a filtered light throughput efficiency $(I/I_o)_e$ (182), or light throughput efficiency (172) as filtered by specific response (162) of the human eye.

FIG. 12 indicates that filtered light throughput efficiency (182) is maximized by light having a wavelength in the approximate range of 610-640 nm, more specifically 615-635 nm. Therefore, light having this range of wavelength will be able to both travel more efficiently through the human body while simultaneously being detected with the human eye at easier rates of visibility. It is important to note that exact optimal wavelength may depend on factors such as, but not limited to, concentration of blood and the amount of melanin. Therefore, the darker the skin, a higher wavelength of light may be more effective.

Light source (112) is capable of emitting light with specific wavelengths. Therefore, light source (112) may emit light with the approximate range of wavelengths, 610-640 nm or more specifically 615-635 nm, establishing a higher filtered light throughput efficiency (182). In turn, light transmitted transcutaneously by illuminating guidewire system (100) may be more visible than light emitted by previous guidewire systems. Various suitable ways in which light source (112) may be modified to provide light within the approximate range of wavelengths, 610-640 nm or more specifically 615-635 nm, will be apparent to those of ordinary skill in the art in view of the teachings herein. It should also be understood that light source (112) may include features enabling the operator to fine tune the wavelength (or wavelengths) of the emitted light, within the above-noted wavelength ranges and/or at least partially outside of the above-noted wavelength ranges. Such ad hoc fine tuning may be desirable to account for anatomical variability among patients, enabling the operator to achieve the best transcutaneous light transmissivity (and, hence, visibility) through the patient at hand.

B. Pulsating Light Source

Figure 13:
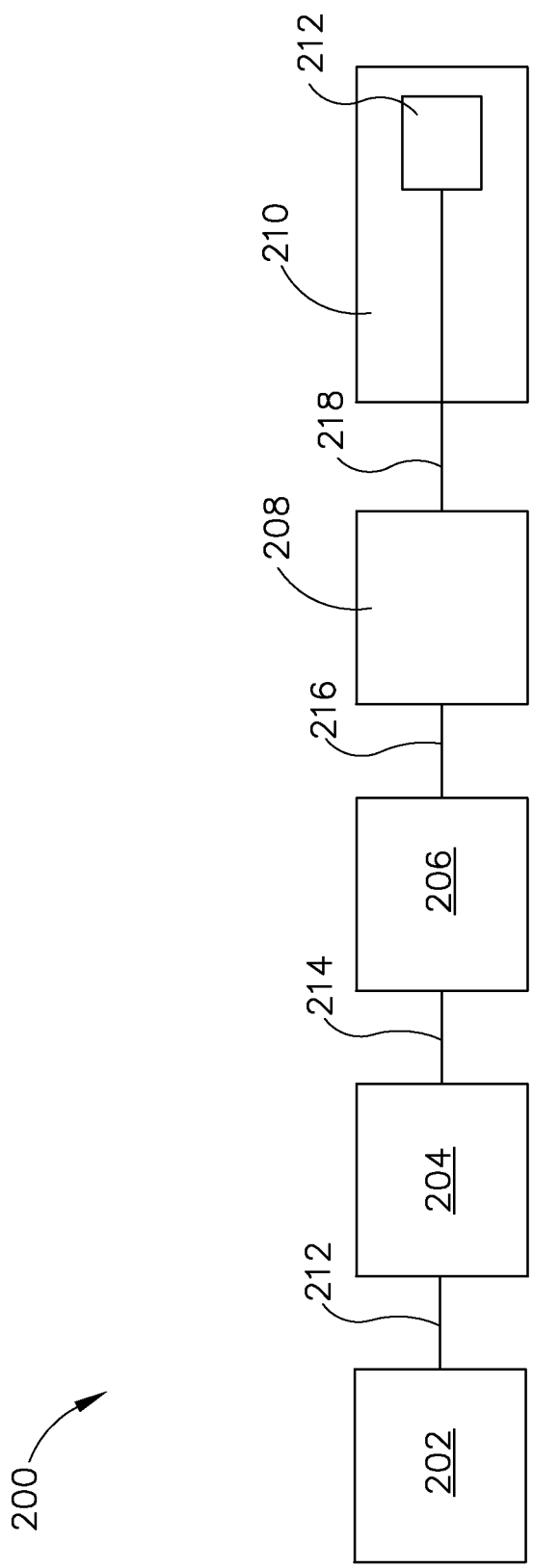
FIG. 13 depicts a schematic diagram of another exemplary illuminating guidewire system with a pulse generator, which may be used with the dilation catheter system of FIG. 1.

FIG. 13 shows another exemplary illuminating guidewire system (200), which includes a power source (202), a pulse generator (204), a light source (206), a connector (208), a guidewire (210), and an illumination fiber (218) traveling through guidewire (210) and connecting to optical lens (212) located at the distal end of guidewire (210). Power source (202) is connected to pulse generator (204) by electrical wiring (214). Pulse generator (204) is also connected to light source (206) by electrical wiring (214). Alternatively, pulse generator (204) may be unitarily coupled to either power source (202) or light source (206). Power source (202) is operable to provide the proper amount of electrical power to activate light source (206).

As described in greater detail below, pulse generator (204) is operable to manipulate the electrical power provided by power source (202) to light source (206). Pulse generator (204) may comprise an electrical circuit including any suitable components as will be apparent to one skilled in the art to manipulate the electrical power provided by power source (202) to light source (206) in view of the teachings herein. Light source (206) is capable of generating light with specific wavelengths as well as "white light" mixture of wavelengths. Alternatively, light source (206) may only generate specific wavelengths, without the capabilities of generating "white light." By way of example only, light source (206) may comprise an LED or a laser diode. Of course, any suitable component for light source may be used as will be apparent to one skilled in the art in view of the teachings herein. Moreover, light source (206) may operate at 5 mW with a light wavelength of 635 nm. Alternatively, other power levels and/or wavelengths may be used. Light source (206) connects to light tube (216), which in turn connects to connector (208). Light tube (216) is capable of communicating light generated by light source (206) to connector (208).

Connector (208) may be substantially similar to both connectors (55, 114) referenced above. Specifically, connector (208) enables optical coupling of illumination fiber (218) with light source (206) and/or light tube (216). Additionally, connector (208) may also be connected to the proximal end of guidewire (210). Guidewire (210) is substantially similar to both guidewires (50, 116) referenced above. Therefore, light generated by light source (206) is capable of traveling through light tube (216), illumination fiber (218), and optical lens (212) to provide transcutaneous illumination through the patient's face to enable an operator to visually confirm positioning of the distal end of guidewire (210) in a patient's sinus cavity. It should therefore be understood that guidewire (210) may be used as a part of dilation catheter system (10) in place of guidewire (50).

As mentioned above, pulse generator (204) is operable to manipulate the electrical power provided by power source (202) to light source (206). When light source (206) provides illumination through lens (212) at a relatively low intensity compared to the ambient background lighting, it may become difficult for an operator to visualize the transillumination effect. The operator's eyes may even adjust to the low intensity light of the transillumination effect from a consistent light provided from light source (206) through lens (212), which may make it even more difficult to visualize the transillumination effect. However, if light source (206) is turned on and off sequentially, then the presence of light emitted from light source (206) through lens (212) may become more noticeable relative to the ambient background lighting.

To achieve the repeated toggling of power to light source (206), pulse generator (204) is operable to convert an otherwise constant stream of electrical power generated by power source (202) into a low frequency pulse of electrical power to light source (206). In particular, pulse generator (204) converts a constant electrical power into pulsed electrical power by rapidly alternating between a zero power level and a predetermined power level at a predetermined frequency. This low frequency pulse may be used to repeatedly turn light source (206) on and off at a specific frequency, through a range of predetermined frequencies in a sequential order, or through a range of predetermined frequencies in a random order. The frequency of the pulse used to turn on and off light source (206) may range from 0.1 Hz to 10 Hz, more specifically around 1 Hz to 3 Hz. This frequency pulse generated by pulse generator (204) may enhance visibility of the transillumination effect to the operator.

Using pulsed energy (i.e., a low duty cycle) to drive light source (206) may enable illuminating guidewire system (200) to drive light source (206) at a higher level of output than could otherwise be achieved through a constant stream of electrical power. The higher level of output would be achieved without damaging light source (206). Pulsing of light source (206) may also improve throughput efficiency, which may enable illumination fibers (218) with smaller diameters to be used. Illumination fibers (218) with smaller diameters may enable guidewire (210) to have a smaller diameter to more easily access tight spaces in the patient's head.

C. Light Source with Synchronous Detection Method

FIG. 14 shows a synchronous detection system (300) including a power source (302), a pulse generator (304), a light source (306), a phase shifter (308), and an electronic shutter (310). Power source (302) is connected to pulse generator (304) via electric wiring (312). Pulse generator (304) is connected to both phase shifter (308) and light source (306) via electric wiring (312). Phase shifter (308) in turn is connected to an electronic shutter (310) via electric wiring (312).

In the current example, electric wiring (312) connecting pulse generator (304) to phase shifter (308) and light source (306) splits, similar to a "Y" connection. However, pulse generator (304) may be connected to phase shifter (308) and light source (306) with two separate lines of electric wiring (312). Alternatively, phase shifter may be integrated within pulse generator (304), pulse generator (304) may be integrated into power source (302), or any suitable combination therefore that would be apparent to a person having ordinary skill in the art in view of the teachings herein.

Power source (302) may be substantially similar to power sources (110, 202) referenced above. Similarly, light source (306) may be substantially similar to light sources (112, 206) referenced above. Light source (306) may include any means of generating light, such as an incandescent lamp, a laser diode, or an LED, etc. Power source (302) is operable to provide electrical power to light source (306), which in turn generates light. Light source (306) may be incorporated into illuminating guidewire systems (100, 200), such that light generated by light source (306) may be capable of traveling through light tube (122, 216), illumination fiber (56, 124, 218), and optical lens (58, 118, 212) to provide transcutaneous illumination through the patient's face to enable an operator to visually confirm positioning of the distal end of guidewire (50, 116, 210) in a patient's sinus cavity. It should therefore be understood that system (300) may be used in combination with dilation catheter system (10) described above, to assist in locating a sinus cavity or other passageway (e.g., frontal recess, etc.) in a patient's head.

Pulse generator (304) is configured to modulate electrical power provided by power source (302) in such a way that the modulated voltage alternates between about zero (i.e. a low voltage) to a predetermined voltage level. Pulse generator (304) may modulate electrical power provided by power source (302) at a predetermined frequency, a range of predetermined frequencies in a specific order, a randomly generated range of frequencies, or any combination thereof. Pulse generator (304) may modulate the electrical power of power source (302) at a frequency greater than that at which the human eye visualizes images, also known as the flicker fusion threshold. This value may be on the order of tens of Hz (e.g., around 60 Hz) depending on the individual. Therefore, the naked human eye may not detect pulse generator (304) modulating the voltage supply of light source (306). As a result, the light provided by light source (306) through lens (58, 118, 212) will seem continuous to the naked human eye, despite the fact that the light is in fact pulsing or flickering. Of course, frequencies lower than 60 Hz may also be utilized.

Electronic shutter (310) may be composed of an electrical shutter glass that is configured to transition from an open state to a closed state (e.g., through polarization) in response to an applied voltage. In particular, electronic shutter (310) will appear to be almost transparent when exposed to a low DC voltage, corresponding to an open state. When electronic shutter (310) is in the open state, light is capable of traveling through electronic shutter (310). Alternatively, electronic shutter (310) will appear to be opaque with when exposed to a DC voltage, corresponding to a closed state. When electronic shutter (310) is in the closed state, light is restricted from traveling through electronic shutter (310). Electronic shutter (310) may also contain a filter within the shutter glass to allow specific wavelengths of light to pass more efficiently as compared to other wavelengths. This may provide benefits if light source (306) emits a specified range of wavelengths rather than "white light."

As mentioned above, pulse generator (304) is also connected to phase shifter (308), which in turn connects to electronic shutter (310). Pulse generator (304) connects to phase shifter (308) in such a manner as to not affect the electrical signal between pulse generator (304) and light source (306). Phase shifter (308) is positioned between electronic shutter (310) and pulse generator (304). Phase shifter (308) is capable of shifting the phase of the voltage pulse stream generated by pulse generator (304) by 180° before delivering the phase shifted voltage to electronic shutter (310). As a result, electronic shutter (310) is exposed to voltage pulses from pulse generator (304) at separate times as compared to light source (306).

This 180° phase offset between voltages is best shown in FIG. 15, which displays the voltage ($V_L$) corresponding to light source (306) as a function of time and the voltage ($V_{es}$) corresponding to electronic shutter (310) as a function of time. While FIG. 15 shows pulse generator (304) as generating voltage pulses (402, 404) in the form of square waves, it should be understood that any other suitable waveform may be used. In the current example, phase shifter (308) provides each voltage pulse (404) to electronic shutter (310) when light source (306) is not receiving a voltage pulse (402). Conversely, phase shifter (308) ensures that electronic shutter (310) is not receiving a voltage pulse (404) when light source (306) receives each voltage pulse (402). While the pulses (402, 404) are provided 180° apart from each other, the frequencies of pulses (404, 404) are the same. When electronic shutter (310) is not receiving a voltage pulse (404), electronic shutter (310) will be in the open state, allowing the light from light source (306) (which is receiving a voltage pulse (402) each time electronic shutter (310) is not receiving a voltage pulse (404)) to travel through electronic shutter (310). Conversely, each time light source (306) does not receive a voltage pulse (402) and thus does not generate a pulse of light, electronic shutter (310) receives a voltage pulse (404) and thus transitions to a closed state, thereby preventing light form traveling through electronic shutter (310).

It should be understood from the foregoing that each moment light source (306) provides a pulse of light, electronic shutter (310) will be in an open state; and each moment light source (306) is not providing a pulse of light, electronic shutter (310) is in a closed state. As noted above, the frequency of the voltage pulses (and, hence, the frequency of the light pulses and shutter activation pulses) are rapid enough to not be discernible to the human eye. Therefore, when the pulsing light is viewed through the pulsing shutter (310), the light will appear to be continuously illuminated.

Electronic shutter (310) may be implemented into eye glasses, goggles, or a screen in front of an operator's eyes. The location of electronic shutter (310) may be positioned to block the ambient light as much as possible. By allowing the electronic shutter (310) to be in a closed state, thereby blocking ambient light from the operator's eyes, when light source (306) is off, the amount of light reaching the eye may be reduced, which may cause the eye pupil to achieve a state of dilation that is higher than it would otherwise achieve without the presence of shutter (310). This higher state of dilation may place the eye at a higher gain such that the eye may see light source (306) better. Utilizing certain modulation frequencies, the pulse generator (304) may further reduce certain ambient light frequencies exposed to the operator's eye, such that the amount of ambient light that reaches the operator's eye may be reduced by shuttering. Utilizing a random frequency generator within the pulse generator (304) may reduce the probability of interference with ambient light with a variety of frequencies (i.e. "white light").

FIGS. 16A-16B show an exemplary operation of synchronous detection system (300) in use. Light source (306) is placed under skin (80) of a patient (e.g., as the distal tip of an illuminating guidewire within a sinus cavity) while electronic shutter (310) is located between an ambient light source (95) and eye (90) of the operator. FIG. 16A shows light source (306) in an activated state. At this moment, pulse generator (304) is currently supplying light source (306) with a voltage pulse (402). Due to phase shifter (308), electronic shutter (310) is simultaneously not receiving a voltage pulse (404), causing electronic shutter (310) to be in an open state. Since electronic shutter (310) is in an open state, light from ambient light (95) and light source (306) are capable of traveling through electronic shutter (310). However, as previously mentioned, a filter may be applied to electronic shutter (310) may only allow specific wavelengths to travel through electronic shutter. Light source (306) may also be configured to only emit the corresponding specific wavelengths of light. In that case, additional wavelengths from ambient light (95) not corresponding with the specific wavelengths will be blocked due to the filter of electronic shutter (310).

FIG. 16B shows light source (306) in a de-activated state. At this moment, pulse generator (304) is not currently supplying light source (306) with a voltage pulse (402). Due to phase shifter (308), electronic shutter (310) is simultaneously receiving a voltage pulse (404), causing electronic shutter (310) to be in a closed state. Since electronic shutter (310) is in a closed state, ambient light (95) is restricted from traveling through electronic shutter (310). Therefore, a limited amount of ambient light (95) impinges on the eye (90) of the operator.

V. Guidewire Orientation Marker

In some instances, it might be desirable to determine the orientation of a guidewire (e.g., guidewire (50)) as it exits the distal end of a guide catheter (e.g., guide catheter (30)). This may be particularly desirable in instances where the guidewire has a preformed bend at the distal end of the guidewire (e.g., at approximately 20°), helping an operator steer the guidewire in different directions by rotating the guidewire about its own axis before advancing the guidewire. In this manner, an operator can steer the tip of the guidewire toward the target anatomical structures. However, for example, when advancing the guidewire around the uncinate process to head toward the maxillary sinus ostium (or along some other tortuous path), it might be difficult to see which direction the preformed bend of the guidewire is pointing in as it exits the guide catheter. This problem is seen in FIG. 19.

Figure 17:
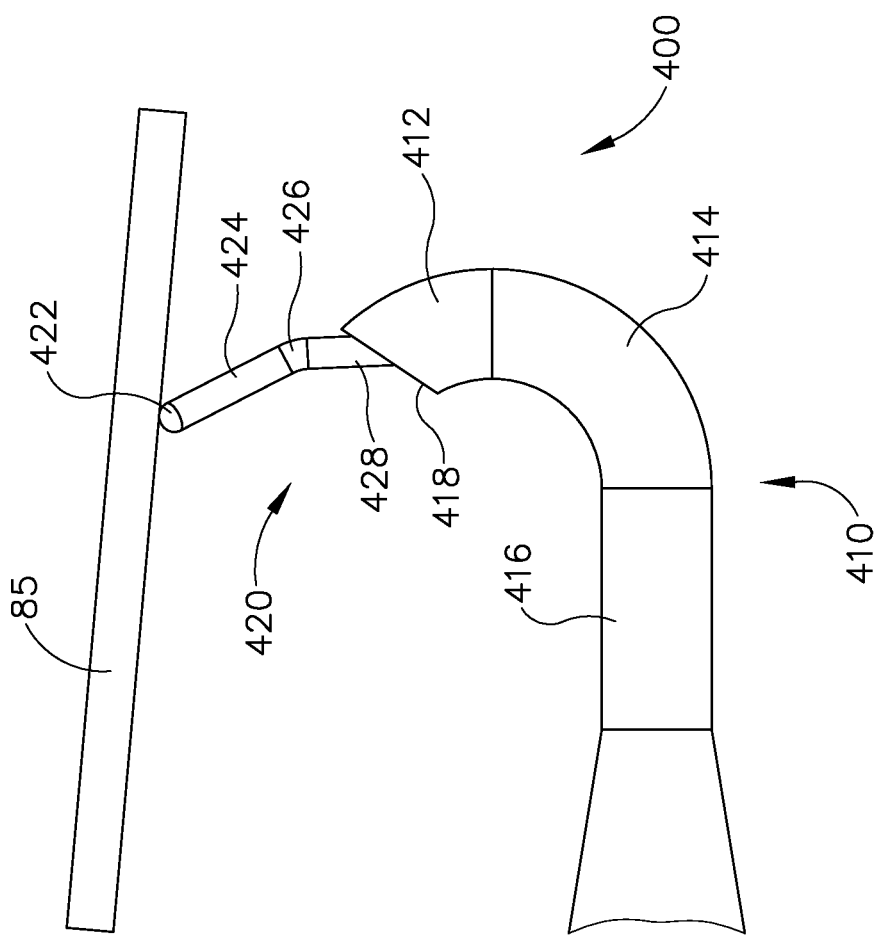
FIG. 17 depicts a side view of the distal end of another exemplary guidewire exiting from the distal end of another exemplary guide catheter while the exemplary guidewire is in a first orientation.
Figure 18:
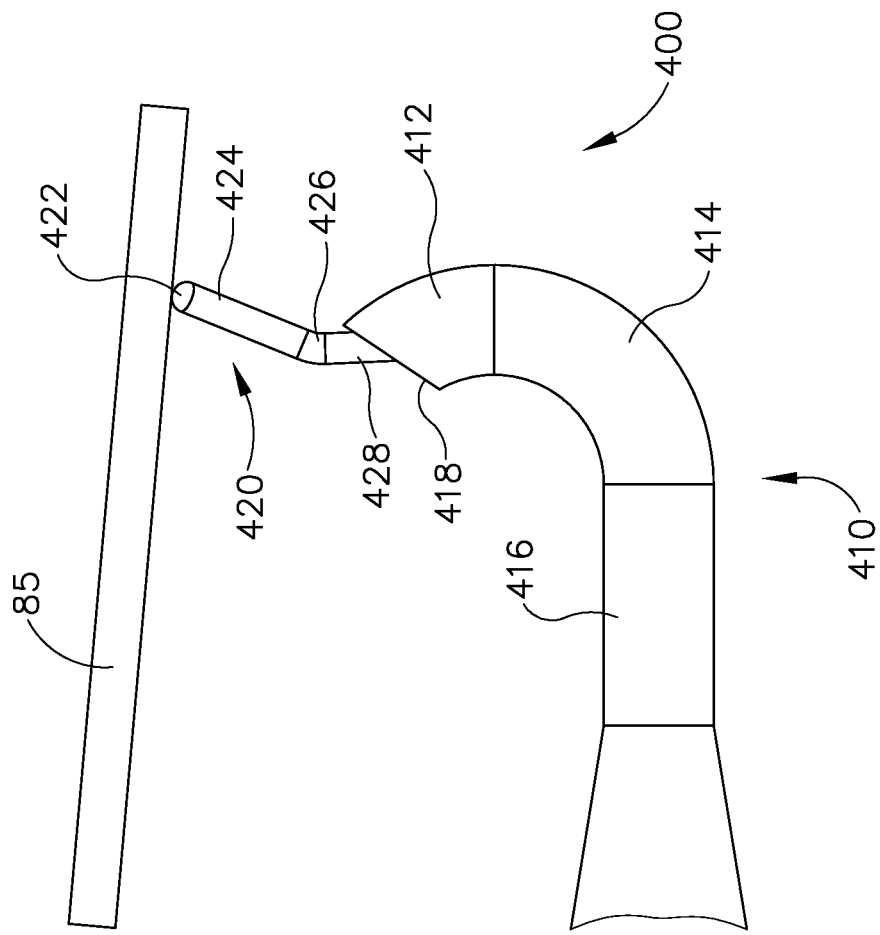
FIG. 18 depicts a side view of the distal end of the guidewire and guide catheter of FIG. 17, where the guidewire is exiting from the distal end of the guide catheter in a second orientation.
Figure 19:
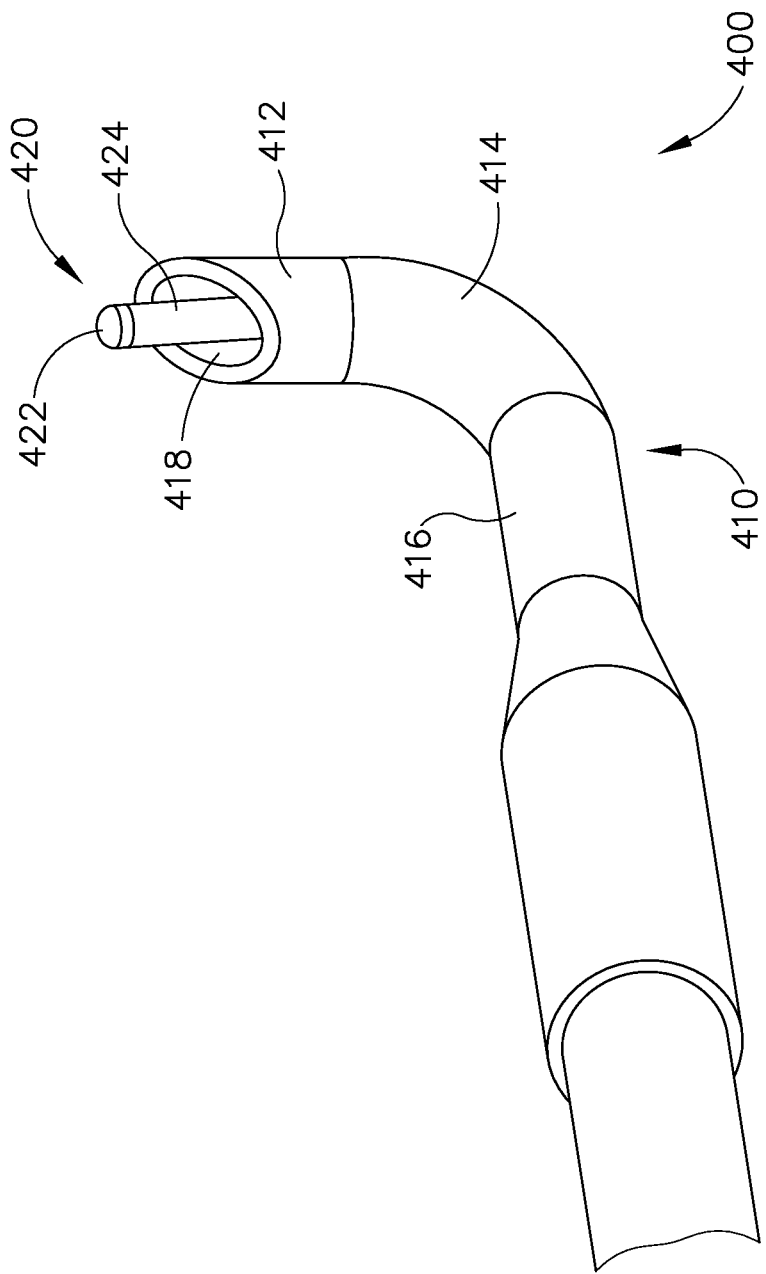
FIG. 19 depicts a perspective view of the distal end of the guidewire and guide catheter of FIG. 17, where the guidewire has yet to exit the distal end of the guide catheter and the orientation of the guidewire is not identifiable.

FIGS. 17-19 show an exemplary guide system (400) including a guide catheter (410) and a guidewire (420). It should be understood that guide catheter (410) and guidewire (420) may be provided as components of a dilation catheter system (10), much like guide catheter (30) and guidewire (50) described above. Guide catheter (410) includes a longitudinal shaft (416), a preformed catheter bend (414), and a guide catheter distal tip (412) defining an exit hole (418) for guidewire (420) to protrude from. Guidewire (420) includes a guidewire proximal end (428), a guidewire distal end (424), a preformed guidewire bend (426) located between proximal end (428) and distal end (424), and an atraumatic tip (422). It should be understood that guidewire (420) may further include various other components as described herein, including but not limited to an illumination fiber (56, 124, 218) and a lens (58, 118, 212). FIG. 19 shows guidewire (420) just exiting exit hole (418) defined by distal tip (412). At this point, it is may be difficult for the operator to determine what direction guidewire bend (426) is facing. Guidewire bend (426) could point atraumatic tip (422) in the correct anterior orientation in relation to anatomical region (85) as depicted in FIG. 17; or guidewire bend (426) could point atraumatic tip (422) in the incorrect posterior orientation in relation to anatomical region (85) as depicted in FIG. 18. Of course, these designations of "correct" and "incorrect" are being provided for merely illustrative purposes only. In some instances, an orientation such as that shown in FIG. 18 may in fact be correct for the particular procedure at hand.

By the time enough of guidewire (420) is advanced past guide catheter (410) to visually confirm the direction of guidewire bend (426), guidewire (420) may be around the uncinate process. As shown in FIG. 17, if guidewire bend (426) is pointed toward the ostium of the maxillary sinus, guidewire (420) may have a better chance of going down the infundibulum and into the ostium. However, as shown in FIG. 18, if guidewire bend (426) is pointed away from the ostium of the maxillary sinus, guidewire (420) may have a greater chance of buckling and/or heading in the wrong direction when advanced further distally out of exit hole (418). Therefore, it might be desirable if an operator could more readily discern which direction guidewire (420) was pointing, which may remove the need for random rotation and searching and thereby reduce the time it takes to find the maxillary sinus.

Figure 20:
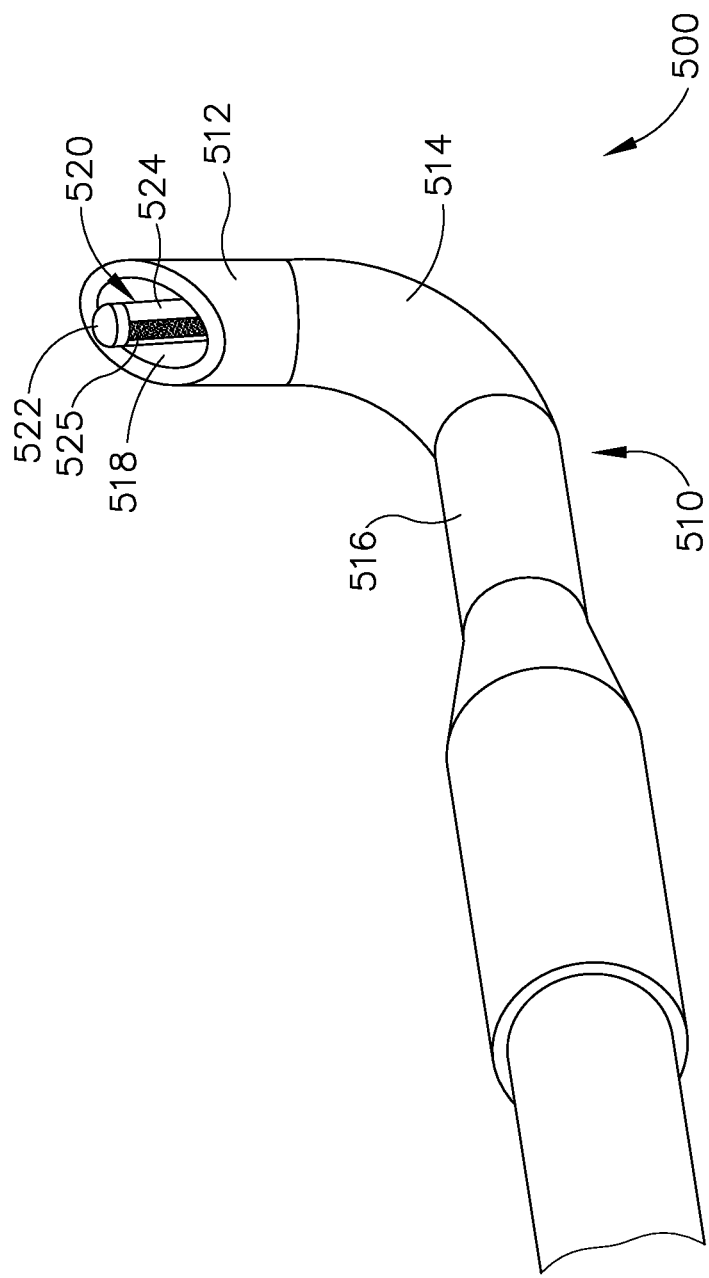
FIG. 20 depicts a perspective view of the distal end of another exemplary guidewire and another exemplary guide catheter, where the guidewire has yet to exit the distal end of the guide catheter and the orientation of the guidewire is identifiable.
Figure 21:
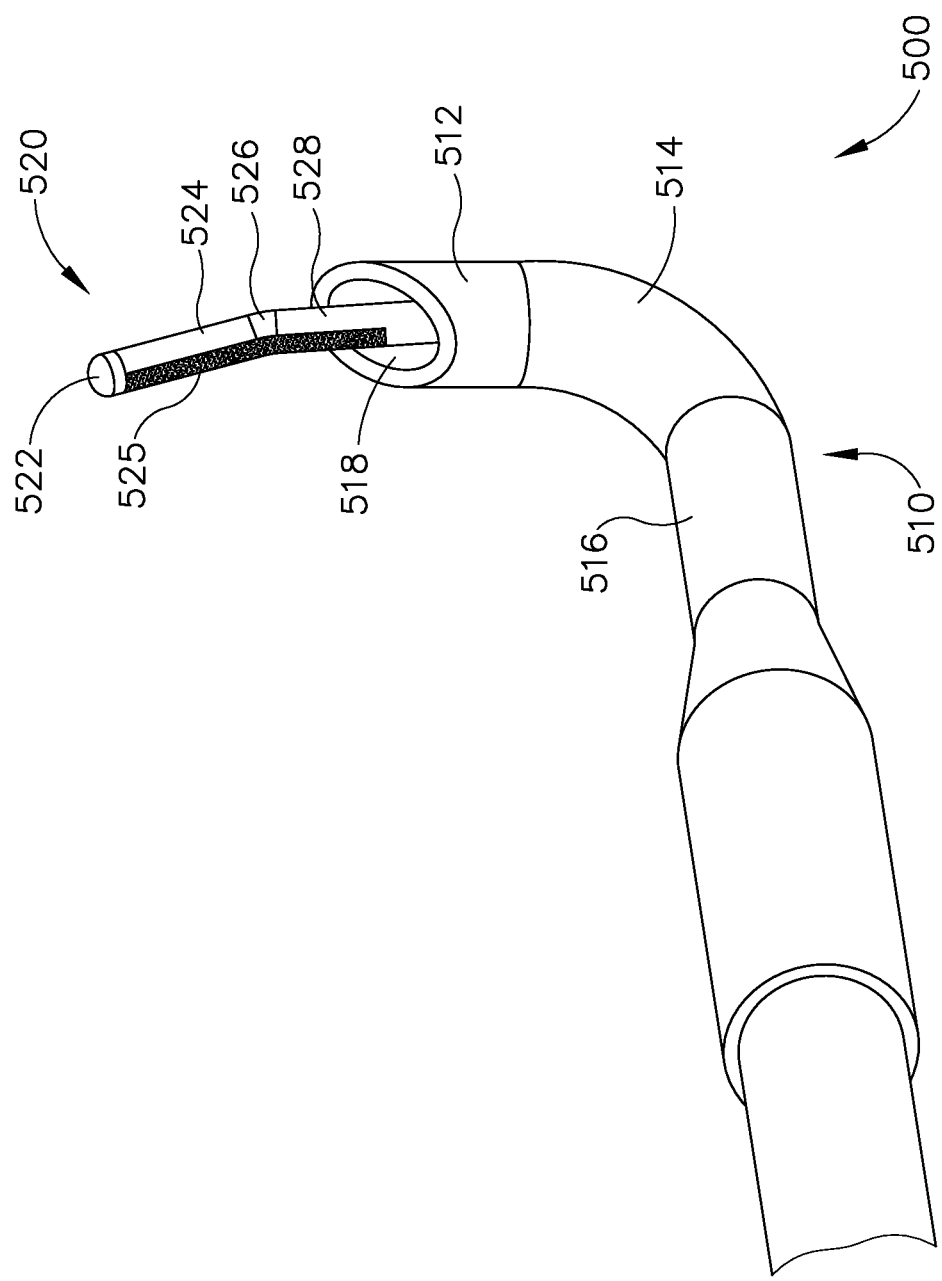
FIG. 21 depicts a perspective view of the distal end of the guidewire and guide catheter of FIG. 20, where the distal end of the guidewire has exited from the distal end of the guide catheter.

FIGS. 20-21 show another guide system (500) including a guide catheter (510) and a guidewire (520). Again, guide catheter (510) and guidewire (520) may be provided as components of a dilation catheter system (10), much like guide catheter (30) and guidewire (50) described above. Guide catheter (510) is substantially similar to guide catheter (410) described above. Guide catheter (510) includes a longitudinal shaft (516), a preformed catheter bend (514), and a guide catheter distal tip (512) defining an exit hole (518) for guidewire (520) to protrude from.

Guidewire (520) is substantially similar to guidewire (420) mentioned above with a difference as will be described below. Guidewire (520) includes a guidewire proximal end (528), a guidewire distal end (524), a preformed guidewire bend (526) located between proximal end (528) and distal end (524), an atraumatic tip (522), and guidewire marker (525) extending from at least a portion of distal end (524). Guidewire marker (525) runs along one section of guidewire (520) in order to indicate the direction which guidewire bend (526) orients guidewire distal end (524). It is noted that guidewire marker (525) is located on the inner radius of guidewire bend (526) in the current example. Alternatively, guidewire marker (525) may be located on the outer radius of guidewire bend (526) in order to serve the same function of indicating orientation of guidewire bend (526). In the present example, guidewire marker (525) is formed by a laser etching process. Alternatively, guidewire marker (525) may be formed in any other suitable fashion.

As shown in FIG. 20, guidewire (520) is just exiting exit hole (518) defined by distal tip (518). In comparison to guide system (400) in a similar position as shown in FIG. 19, guidewire marker (525) makes it easy to for the operator to determine what direction guidewire bend (526) is facing simply by observing guidewire marker (525). The operator now has visual confirmation on what direction guidewire (520) will exit from exit hole (518). If the operator does not see guidewire marker (525) at the stage depicted in FIG. 20, the operator may rotate guidewire (520) within guide catheter (510) until the operator sees guidewire marker (525) in the position shown in FIG. 20. This rotation of guidewire (520) within guide catheter (510) may be performed without necessarily advancing guidewire (520) any further distally from the position shown in FIG. 20. It should also be understood that the presence of guidewire marker (525) may be visually observed using an instrument such as endoscope (60) and/or using any other suitable devices or techniques.

VI. Disposable LED Light Source

In some instances, it may be desirable to utilize a light source directly coupled to an illumination guidewire (e.g., guidewire (50)). Attaching a light source directly to an illumination guidewire may result in a stronger luminance at the distal end of a guidewire due to a reduced loss of luminal energy stemming from shorter travel distance between light source and guidewire. This could lead to less power requirements for an illumination system.

Figure 22:
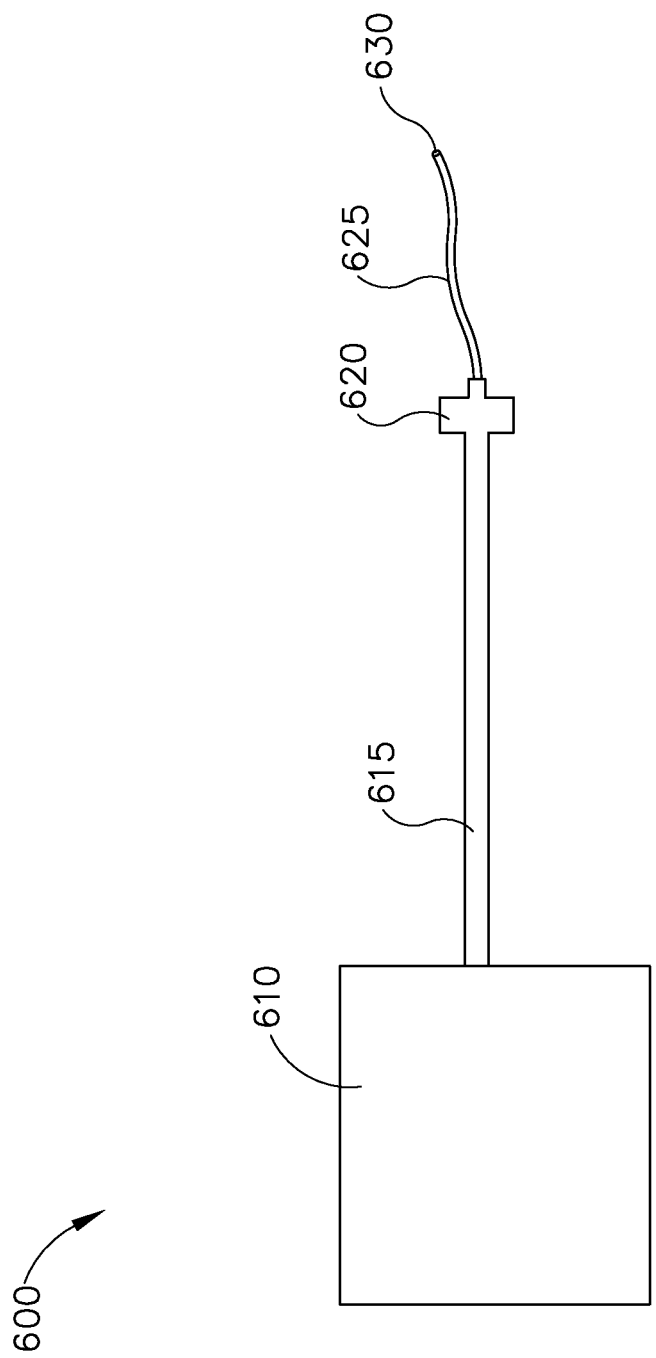
FIG. 22 depicts a side view of an exemplary illuminating guidewire system that may be used with the dilation catheter system of FIG. 1.

FIG. 22 shows an exemplary illuminating guidewire system (600) including a light source (610), a light tube (615), a connector (620), a guidewire (625), and an optical lens (630). In some instances, light source (610) is bulky and requires light tube (615) in order to provide optical communication between light source (610) and connector (620). Connector (620) may be substantially similar to connectors (55, 114, 208) referenced above. Guidewire (625) may be substantially similar to guidewires (50, 116, 210, 420, 520) mentioned above. Light travels from light source (610), through light tube (615), and into guidewire (625) via connector (620).

Figure 23:
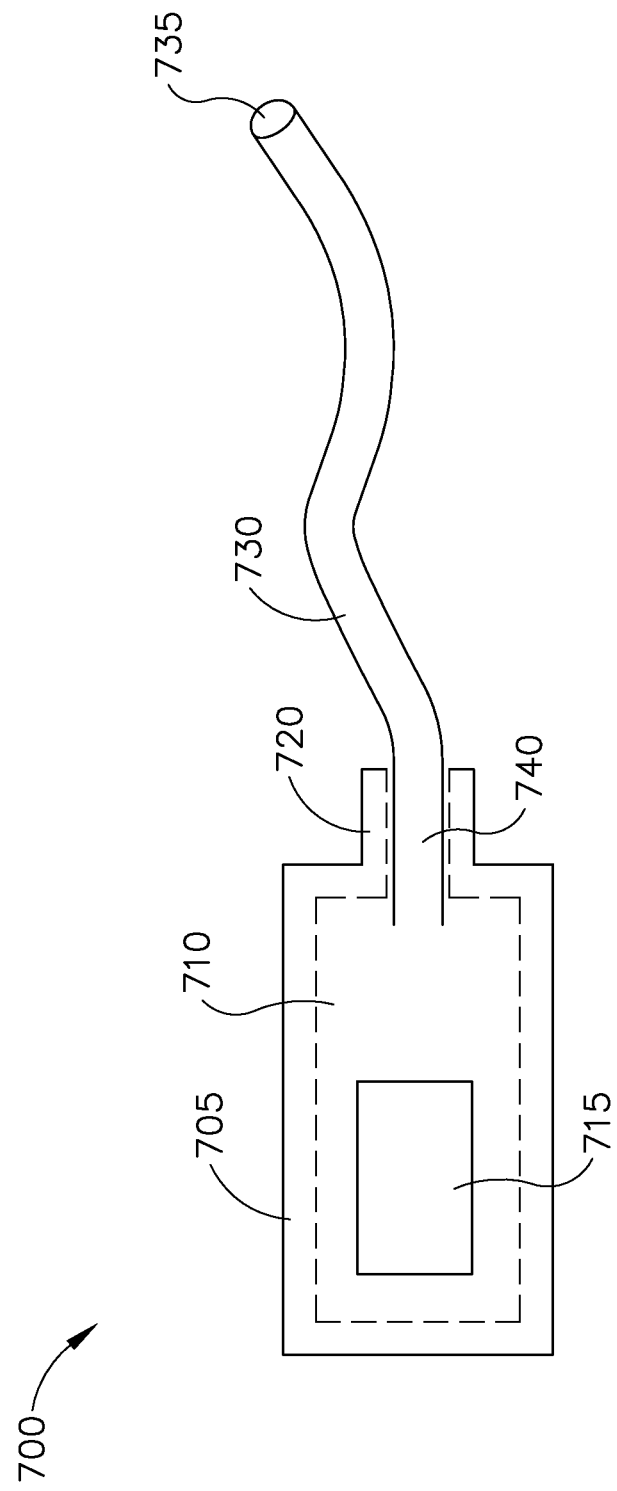
FIG. 23 depicts a side view of another exemplary illuminating guidewire system that may be used with the dilation catheter system of FIG. 1.

However, FIG. 23 shows an exemplary alternative illuminating guidewire system (700) that includes a casing (705) unitarily coupled to connector (720), a light source (715) integrally located within a cavity (710) defined by casing (705), a guidewire (730) attached to connector (720) at the proximal end (740) of guidewire (730), and an optical lens (735) located at the distal end of guidewire (730). In this example, connector (720) is also partially defined by cavity (710). Because light source (715) is disposed within cavity (710) defined by casing (705), and connector (720) is unitarily coupled to casing (705), there is no longer a need for light tube (615). Eliminating light tube (615) reduces the length that light must travel from light source (715) to optical lens (735) while simultaneously reducing the size of light source (715) by unitarily coupling casing (705) with connector (720). With reduced size and reduced amount of components, casing (705), connector (720) and light source (715) may be disposable and/or more compact.

As yet another merely illustrative example, a light source such as light source (715) may be directly integrated into a handle assembly of a sinuplasty instrument system. This may eliminate the need for coupling a light conduit between the handle assembly and an external light source in order to provide illumination through a guidewire like guidewire (730). By way of example only, the light source may be integrated into a handle assembly like any of the various handle assemblies described in U.S. Pub. No. 2012/0071856, entitled "Medical Device and Method for Treatment of a Sinus Opening," published Mar. 22, 2012, now U.S. Pat. No. 9,554,817, issued Jan. 31, 2017, the disclosure of which is incorporated by reference herein; and/or U.S. Pub. No. 2014/0107427, entitled "Balloon Dilation Catheter System for Treatment and Irrigation of the Sinuses," published Apr. 17, 2014, now U.S. Pat. No. 9,579,448, issued Feb. 28, 2017, the disclosure of which is incorporated by reference herein.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a power source; (b) a pulse generator in electrical communication with the power source, wherein the pulse generator is operable to generate an electric pulse; (c) a light source in electrical communication with the pulse generator, wherein the light source is operable to turn on and off based on the electric pulse received from the pulse generator; (d) a guidewire comprising a first proximal end and a first distal end; (e) an optical fiber extending within the guidewire from the first proximal end toward the first distal end, wherein the optical fiber comprises a second proximal end and a second distal end; and (f) a connector operable to couple with the first proximal end of the guidewire, wherein the connector is operable to allow the light source to communicate with the optical fiber.

Example 2

The apparatus of Example 1, wherein the pulse generator is configured to generate the electrical pulse at a low frequency.

Example 3

The apparatus of either Example 2, wherein the pulse generator is configured to generate the electrical pulse within a range from about 0.1 Hz to 10 Hz.

Example 4

The apparatus of Example 2, wherein the pulse generator is configured to generate the electrical pulse within a range from about 1 Hz to 3 Hz.

Example 5

The apparatus of any one or more of Examples 1 through 4, wherein the light source is operable to generate light having a specific wavelength within the range of about 610 nm to about 640 nm.

Example 6

The apparatus of any one or more of Examples 1 through 5, wherein the pulse generator is configured to generate a pulse with a frequency equal to or greater than 60 Hz.

Example 7

The apparatus of any one or more of Examples 1 through 6, wherein the apparatus further comprises: (a) a phase shifter in electrical communication with the pulse generator; and (b) an electrical shutter in communication with the phase shifter.

Example 8

The apparatus of Example 7, wherein the electrical shutter is operable to transition between an open state and a closed state, wherein the electrical shutter is configured to allow light to pass through the shutter in the open state, wherein the electrical shutter is configured to restrict the passage of light in the closed state.

Example 9

The apparatus of Example 8, wherein the electrical shutter is operable to be in the open state when exposed to a voltage, wherein the electrical shutter is operable to be in the closed state when exposed to a low voltage.

Example 10

The apparatus of any one or more of Examples 8 through 9, wherein the electrical shutter further comprises a filter, wherein the filter is operable to allow specific wavelengths of light to pass through the shutter regardless of the shutter being in the open state or the closed state.

Example 11

The apparatus of any one or more of Examples 7 through 10, wherein the phase shifter is configured to shift the signal generated by the pulse generator by 180 degrees in comparison to the signal received by the light source.

Example 12

The apparatus of any one or more of Examples 7 through 11, wherein the electrical shutter comprises a set a goggles or glasses.

Example 13

The apparatus of any one or more of Examples 7 through 11, wherein the electrical shutter comprises a screen.

Example 14

The apparatus of any one or more of Examples 1 through 13, wherein the pulse generator is configured to generate a random frequency pulse continuously above 60 Hz.

Example 15

The apparatus of any one or more of Examples 1 through 14, wherein the light source comprises an LED.

Example 16

The apparatus of any one or more of Examples 1 through 14, wherein the light source comprises a laser diode.

Example 17

An apparatus comprising: (a) a light source; (b) an optical fiber in optical communication with the light source; (c) a guidewire, wherein the optical fiber extends through the guidewire, wherein the guidewire includes a distal end, wherein the optical fiber is configured to emit light from the light source through the distal end of the guidewire; (d) a viewing apparatus comprising an electrically actuated shutter; and (e) a controller, wherein the controller is operable to provide pulsed light from the light source through the optical fiber, wherein the controller is further operable to control the shutter of the viewing apparatus in synchronization with the pulsed light from the light source.

Example 18

A method of providing transillumination through a patient's face, the method comprising: (a) inserting an illuminating guidewire into a paranasal sinus cavity of the patient, wherein the illuminating guidewire has a distal end operable to emit light; and (b) communicating pulsed light through the distal end of the illuminating guidewire within the sinus cavity, wherein the pulsed light is visible through the patient's face.

Example 19

The method of Example 18, wherein the act of communicating pulsed light comprises pulsing the light at a frequency in the range of about 0.1 Hz to 10 Hz.

Example 20

The method of any one or more of Examples 18 through 19, further comprising activating a shutter in a viewing device to selectively enable viewing through the viewing device, wherein the shutter is activated at the same frequency at which the communicated light is pulsed.

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A guide system comprising:
    (a) a guide catheter comprising:
        (i) a proximal end,
        (ii) a distal end, and
        (iii) a lumen extending from the proximal end to the distal end; and
    (b) a guidewire extending within the lumen of the guide catheter, wherein the guidewire comprises:
        (i) a proximal end,
        (ii) a distal end,
        (iii) a preformed bend formed near the distal end of the guidewire, and
        (iv) a visible marker positioned on or near the preformed bend, wherein the visible marker visually indicates a direction of the preformed bend.

2. The guide system of claim 1, wherein the guide catheter further comprises a longitudinal shaft.

3. The guide system of claim 1, wherein the guide catheter further comprises a preformed catheter bend.

4. The guide system of claim 3, wherein the preformed bend of the guide catheter is approximately 20°.

5. The guide system of claim 1, wherein the visible marker extends proximally from the distal end of the guidewire along the preformed bend.

6. The guide system of claim 1, wherein the guidewire is configured to translate relative to the guide catheter to thereby position the distal end of the guidewire distally in relation to the distal end of the guide catheter.

7. The guide system of claim 6, wherein the guidewire is configured to translate relative to the guide catheter to thereby position the preformed bend of the guidewire distally in relation to the distal end of the guide catheter.

8. The guide system of claim 6, wherein the guidewire is configured to translate relative to the guide catheter to thereby position at least part of the visible marker of the guidewire distally in relation to the distal end of the guide catheter.

9. The guide system of claim 1, further comprising a dilation catheter slidably disposed along the guidewire, wherein the dilation catheter includes an expandable dilator.

10. The guide system of claim 9, wherein the dilation catheter is slidably disposed in the lumen of the guide catheter.

11. The guide system of claim 1, wherein the guidewire further comprises an atraumatic tip.

12. The guide system of claim 1, wherein the visible marker runs along only one side of the guidewire.

13. The guide system of claim 1, wherein the visible marker is located on an inner radius of the guidewire bend.

14. The guide system of claim 1, wherein the visible marker is located on an outer radius of the guidewire bend.

15. The guide system of claim 1, wherein the guide catheter is rigid.

16. The guide system of claim 1, wherein the guidewire is further configured to emit light through the distal end of the guidewire.

17. The guide system of claim 1, wherein the guidewire is rotatable relative to the guide catheter.

18. An apparatus comprising:
    (a) a guide catheter comprising:
        (i) a proximal end,
        (ii) a distal end, and
        (iii) a lumen extending from the proximal end to the distal end; and
    (b) a guidewire extending within the lumen of the guide catheter from the first proximal end to the first distal end, wherein the guidewire comprises:
        (i) a proximal end,
        (ii) a distal end,
        (iii) a preformed bend formed near the distal end of the guidewire, and
        (iv) a visible marking positioned on only either an inner radius of the preformed bend or an outer radius of the preformed bend; and
    (c) a dilation catheter slidably disposed along the guidewire, the dilation catheter including an expandable dilator.

19. A method of orienting a guidewire, the method comprising:
    (a) inserting a marked guidewire into a head of a patient, wherein the marked guidewire comprises a preformed bend and a visible marker indicating a bend direction of the preformed bend;
    (b) rotating the guidewire until the visible marker can be visually observed to indicate that a distal end of the guidewire is oriented for insertion into a targeted anatomical passageway in the head of the patient; and
    (c) advancing the guidewire distally into the targeted anatomical passageway.

20. The method of claim 19, wherein a presence of the visible marker is observed using an endoscope.

* * * * *